United States Patent
Hacker et al.

(10) Patent No.: US 6,221,809 B1
(45) Date of Patent: Apr. 24, 2001

(54) HERBICIDAL COMPOSITIONS COMPRISING N-[(4,6-DIMETHOXYPYRIDIN-2-YL)AMINOCARBONYL]-5-METHYLSULPHONAMIDOMETHYL-2-ALKOXYCARBONYLBENZENE SULPHONAMIDES

(75) Inventors: Erwin Hacker, Hochheim; Hermann Bieringer, Eppstein; Klaus Lorenz, Weiterstadt, all of (DE)

(73) Assignee: Hoechst Schering AgrEvo GmbH, Berlin (DE)

( * ) Notice: Subject to any disclaimer, the term of this patent is extended or adjusted under 35 U.S.C. 154(b) by 0 days.

(21) Appl. No.: 09/319,294

(22) PCT Filed: Nov. 18, 1997

(86) PCT No.: PCT/EP97/06416

§ 371 Date: Oct. 11, 1999

§ 102(e) Date: Oct. 11, 1999

(87) PCT Pub. No.: WO98/24320

PCT Pub. Date: Jun. 11, 1998

(30) Foreign Application Priority Data

Dec. 7, 1996 (DE) ............................................ 196 50 955

(51) Int. Cl.[7] .......................... A01N 43/54; C07D 239/02
(52) U.S. Cl. ........................................... 504/136; 544/312
(58) Field of Search .............................. 504/136; 544/312

Primary Examiner—Jose' G. Dees
Assistant Examiner—Alton Pryor
(74) Attorney, Agent, or Firm—Frommer Lawrence & Haug LLP

(57) ABSTRACT

Herbicidal composition, comprising

A) at least, one compound from the group of the substituted phenylsulfonylureas of the formula I and agriculturally acceptable salts thereof

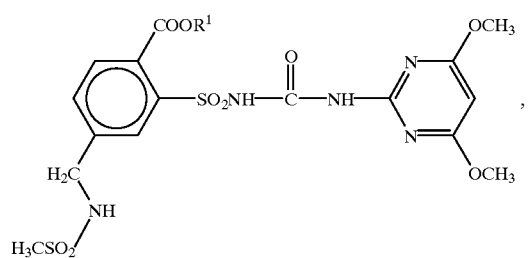

and B) at least one herbicidally active compound selected from the group of the compounds consisting of Ba) herbicides which have selective activity against grasses in cereals,.

Bb) herbicides which have selective activity against dicotyledons in cereals,

Bc) herbicides which have selective activity against grasses and dicotyledons in cereals and Bd) herbicides which are active against weed grasses and broad-leaved weeds and which are nonselective in non-crop areas or perennial crops (plantations) and/or selective in transgenic crops.

38 Claims, No Drawings

HERBICIDAL COMPOSITIONS COMPRISING N-[(4,6-DIMETHOXYPYRIDIN-2-YL)AMINOCARBONYL]-5-METHYLSULPHONAMIDOMETHYL-2-ALKOXYCARBONYLBENZENE SULPHONAMIDES

This appln. is a 371 of PCT/EP9706416 filed Nov. 18, 1997.

The invention relates to the technical field of crop protection agents, in particular to herbicidal compositions comprising N-[(4,6dimethoxypyrimidin-2-yl)aminocarbonyl]-5-methylsulfonamidomethyl-2-alkoxycarbonylbenzenesulfonamides and/or salts thereof.

WO 95/10507 (PCT/EP94/03369) discloses phenylsulfonylureas of the formula I and salts thereof

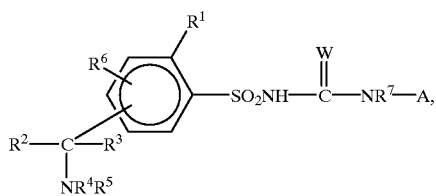

(1)

where the formula 1, owing to the extensive and wide definition of the radicals A, W, $R^1$, $R^2$, $R^3$, $R^4$, $R^5$, $R^6$ and $R^7$, includes a large number of possible individual compounds.

Table 1 of WO 95/10507 lists compounds of the formula 1a

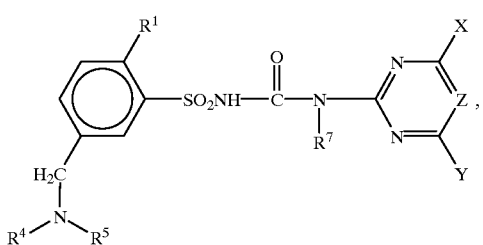

1a)

the examples having the numbers 105, 209, 217, 395, 399, 403, 407, 497 and 536 relating to those compounds of the formula 1 a where Z is CH, X and Y are methoxy, $R^7$ is hydrogen, $R^1$ is alkoxycarbonyl, $R^4$ is hydrogen and $R^5$ is a radical containing a sulfonyl group ($SO_2$ $CH_3$, $SO_2NHCH_3$, $SO_2N(CH_3)_2$, $SO_2$ $N(CH_3)_2$, $SO_2CH_2F$, $SO_2CF_3$, $SO_2C_2H5$, $SO_2$-n-$C_3H_7$, $SO_2CH_3$ or $SO_2CH_3$). However, the melting point is only given for Examples 105 ($R^1$=methoxycarbonyl, $R^5$=methylsulfonyl) and 217 ($R^1$=methoxycarbonyl, $R^5$=$SO_2N(CH_3)_2$) and for Example 536 (sodium salt of the compound 105).

In WO 95/10507, biological examples for the compounds mentioned individually above are given insofar as it is stated in general terms that the compounds of Examples 105, 217 and 536—in addition to a series of other compounds—have very good activity against harmful plants such as Sinapis alba, Stellaria media, Chrysanthemum segetum and Lolium multiflorum in the pre- and post-emergence method at an application rate of 0.3 kg to 0.005 kg of active substance per hectare. The crop plant safety of the compounds of the formula 1 is not documented by examples in the International Published Specification mentioned.

Furthermore, general mention is made of the possibility that the compounds of the formula 1 can be applied together with other herbicides. This mention is followed by an exemplary list of more than about 250 different standard active compounds of which, inter alia, amidosulfurone, bentazone, bifenox, bromoxynil, cafentrazon (ICI-A0051), chlortoluron, chlorsulfuron, clodinafop and its ester derivatives (for example clodinafop-propargyl), dicamba, dichlorprop, diclofop and its esters such as diclofop-methyl, difenzoquat, diflufenican, fenoxaprop and fenoxaprop-P and esters thereof such as, for example, fenoxaprop-P-ethyl and fenoxaprop-ethyl, flamprop-methyl, fluoroglycofen-ethyl, fluroxypyr, flurtamone, fomesafen, glufosinate, glyphosate, imazamethabenz-methyl, ioxynil, isoproturon, lactofen, MCPA, mecoprop, methabenzthiazuron, metribuzin, metsulfuron-methyl, pendimethalin, prosulfocarb, thifensulfuron-methyl, tralkoxydim, triasulfuron and tribenuron-methyl are explicitly mentioned. Other than just mentioning the substances, WO 95/10507 does not provide additional information with regard to the particular essence and purpose of a joint application, nor does it provide a reason for the intended selection and combination of particular active compounds.

Most phenylsulfonylureas disclosed in formula 1 and 1a of WO 95/10507 have useful to good activity against a broad spectrum of economically important mono- and dicotyledonous harmful plants, and active compounds of the formula 1 or 1 a also allow control of weeds encountered in rice under the specific cultivation conditions such as, for example, Sagittaria, Alisma, Eleocharis, Scirpus, Cyperus, etc., however, in many cases the individual active compounds are not sufficient to control the range of mono- and dicotyledonous weeds encountered in agricultural practice in particular in cereals or maize, but also in other crop species.

With respect to the prior art mentioned and discussed herein, it was therefore an object of the invention to provide novel mixtures having herbicidal activity to enable the expert to control, with a single application or a small number of applications of herbicides in cereals and other crop species, the range of weeds or specific weeds which are difficult to control. Furthermore, the mixtures of herbicidal active compounds which are known in principle are meant to contribute to close so-called "activity gaps" and, if possible, to reduce at the same time the application rates of the individual active compounds and to increase flexibility in the timing of the application.

This object, and other objects which have not been specifically mentioned, is achieved by herbicidal compositions having the features of in claim 1. Thus, the invention provides herbicidal compositions, comprising A) at least one herbicidal active compound from the group of the substituted phenylsulfonylureas of the formula I and agriculturally acceptable, i.e. safe or usable, salts thereof

I)

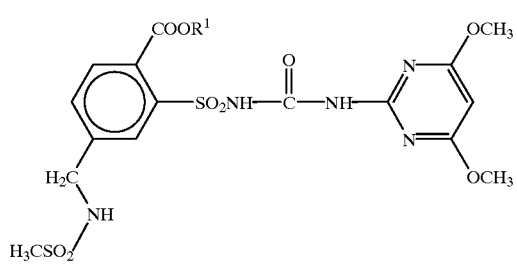

2)

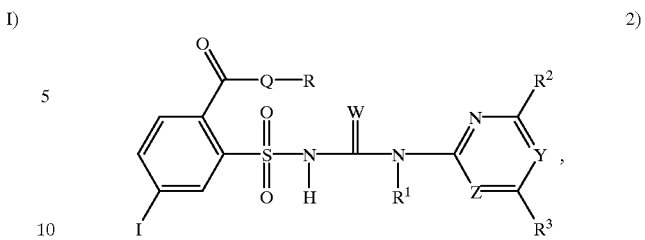

in which

R¹ is $(C_1-C_8)$-alkyl, $(C_3-C_4)$-alkenyl, or $(C_3-C_4)$-alkynyl or $(C_1-C_4)$-alkyl which is mono- to tetra-substituted by radicals selected from the group consisting of halogen and $(C_1-C_2)$-alkoxy, and B) at least one herbicidally active compound selected from the group of the compounds consisting of Ba) herbicides which have selective activity against grasses in cereals, Bb) herbicides which have selective activity against dicotyledons in cereals, Bc) herbicides which have selective activity against grasses and dicotyledons in cereals and Bd) herbicides which are active against weed grasses and broad-leaved weeds and which are nonselective in non-crop areas or perennial crops (plantations) and/or selective in transgenic crops.

The combinations of herbicidally active compounds of types A and B according to the invention permit, in a particularly advantageous manner, the control of the range of weeds required by the expert, even including certain species which are difficult to control. In addition, using the combinations according to the invention it is possible to reduce the active compound application rates of the individual combination partners which are comprised in the combination, thus allowing more economical approaches by the user. Finally, in a not readily foreseeable way, it was possible to achieve increases in activity which surpassed expectations, the herbicidal compositions according to the invention thus showing extensive synergistic effects.

Furthermore, it was particularly surprising in the context of the invention that the sulfonylureas of the formula I carrying a methylsulfonamidomethyl substituent in position 5 of the phenyl ring in combination with other herbicides proved to be outstandingly suitable for the effective control of weed species which are difficult to control. In particular, unexpected specific activities against resistant weed grasses were observed.

Altogether, the quality of the activities found for the combinations according to the invention is generally also better than for example that found for similar combinations comprising sulfonylureas of the closest prior art, as represented for example by phenylsulfonylureas carrying iodine substituents in position 4 of the phenyl ring according to formula 2 of WO 92/13845 where the radicals according to the prior art in formula 2 are, inter alia, Q=O, R=methyl, W=O, R¹=H, R²=OCH₃, R³=CH₃, Z and Y=N.

With respect to the specifically substituted phenylsulfonylureas of the formula I according to the invention it has to be stated that they are in principle embraced for example by the formula 1 of WO 95/10507, but that their outstanding suitability as combination partners for synergistic mixtures with other herbicides is not evident from the prior art. In particular, there are no indications in the known literature that the narrow and clearly defined group of the N-[(4, 6-dimethoxypyrimidin-2-yl)aminocarbonyl]-5-methylsulfonamidomethyl-2-alkoxycarbonylbenzenesulfonamides, which may be present in the form of their salts, occupies such an exceptional position. Likewise, neither the application rates nor the ratios of the amounts of the individual compounds to be employed in the combinations according to the invention are evident from the prior art. Finally, the combinations according to the invention are advantageous in comparison with other herbicidal combinations comprising similar sulfonylureas.

Particularly interesting combination partners of type A for the combinations according to the invention are compounds of the formula I or salts thereof where R¹ is methyl, ethyl, n- or isopropyl, n-, tert-, 2-butyl or isobutyl, n-pentyl, isopentyl, n-hexyl, isohexyl, 1,3-dimethylbutyl, n-heptyl, 1-methylhexyl or 1,4-dimethylpentyl.

In a very particularly preferred embodiment, herbicidal compositions according to the invention comprise a type A compound of the formula I or a salt thereof in which R¹ is methyl.

The compounds of type A (formula 1) can form salts where the hydrogen of the SO₂—NH—CO— group is replaced by an agriculturally suitable cation. These salts are, for example, metal, in particular alkali metal salts (for example sodium or potassium salts) or alkaline earth metal salts, or else ammonium salts or salts with organic amines. Likewise, salt formation can occur by addition of a strong acid to the heterocycle moiety of the compounds of the formula 1. Suitable for this purpose are, for example, HCl, HNO₃, trichloroacetic acid, acetic acid or palmitinic acid.

Particularly advantageous type A compounds are those where the salt of the herbicide of the formula (I) is formed by replacing the hydrogen of the —SO₂—NH—CO— group by a cation selected from the group of the alkali metals, alkaline earth metals and ammonium, preferably sodium.

Even if the compounds of the formula I contain one or more asymmetric carbon atoms or else double bonds which are not specifically indicated in the general formula, they nevertheless belong to the type A compounds. The stereoisomers which are possible and which are defined by their specific spatial form, such as enantiomers, diastereoisomers, Z isomers and E isomers, are all embraced by formula I, and they can be obtained from stereoisomer mixtures by customary methods, or else be prepared by stereoselective reactions in combination with the use of stereochemically pure starting materials. Thus, the mentioned stereoisomers can be employed according to the invention in pure form or else as their mixtures.

The combination partners of type B are generally standard herbicides which are, however, selected according to certain criteria. Thus, except for two (subgroup Bd)), they are herbicides which act selectively against undesirable plants in cereals. The harmful plants to be controlled include in particular grasses and/or dicotyledons. Grasses which are to be particularly controlled include, inter alia, Alopecurus myosuroides, Avena fatua, Apera spica venti, Lolium ssp., Phalares ssp., Setaria ssp., Agropyron repens, Bromus ssp., Sorghum ssp.; dicotyledonous harmful plants which can be controlled particularly effectively include, inter alia, Lamium ssp., Veronica ssp., Viola ssp., Stellaria media, Matricaria ssp., Galium aparine, Sinapis album, Raphanus raphanistrum, Myosotes arcensis, Polygonum ssp., Chenopodium ssp., Rochia ssp./Cirsium, Galeopsis tetra., Capsella bursa pastoris, Paphaver rhoeas, Physallis angulata, Brassica napus, Descurainia richardsonii, Oxalis ssp.; the combinations according to the invention have particularly favorable activity inter alia in the control of Lolium multiflorum, Avena fatua, Apera spica venti, Galium aparine, Oxalis spp, Phalaris minor, Descurainia richardssonii, Capsella bursa pastoris, Polygonum convovulus, Chenopdium album, Paphaver rhoeas, Physalis angulata, Brassica napus, Lamium purpreum, Kochia scorp., etc.

With regard to the activity of the standard herbicides of type B it is in turn possible to grade or classify them with respect to the plants which are controlled most effectively. Thus, some of the type B herbicides are effective almost exclusively against grasses, others predominantly against dicotyledons, whereas the herbicides of type B from subgroup Bc) are employed both against grasses and against dicotyledons. However, in each case an optimized activity spectrum results for the combinations according to the invention by complementation and intensification of the herbicidal properties of the compounds of type A which, on their own have a particularly advantageous range of properties in the control of harmful plants in cereals. Last, but not least, the intensification and complementation of the activity spectrum also applies to the type B compounds of group Bd), which includes the herbicides which are active against weed grasses and broad-leaved weeds and which are non-selective in non-crop areas or in perennial crops (plantations) and/or selective in transgenic crops.

In a preferred variant, a composition according to the invention is characterized in that it comprises, as herbicide (s) of type B, one or more herbicides which have selective activity against grasses in cereals and which are selected from the group consisting of the 2-(4-aryloxyphenoxy) propionic acids and esters thereof, ureas, cyclohexanedione oximes, arylalanins, 2,6-dinitroanilins, imidazolinones and difenzoquat. In addition to the individual substances mentioned, the classes of chemical substances mentioned include a number of grass herbicides which are suitable as combination partners of the compounds of type A.

Preferred compositions according to the invention comprise, as herbicides of type B, one or more herbicides which have selective activity against grasses in cereals and which are selected from the group consisting of B1) fenoxaprop, fenoxaprop-P

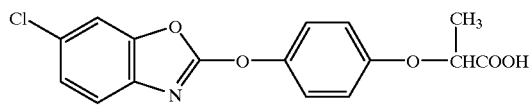

(±) -2-[4-(6-chloro-1,3-benzoxazol-2-yloxy)phenoxy] propionic acid, including, inter alia, the use form as fenoxaprop-ethyl

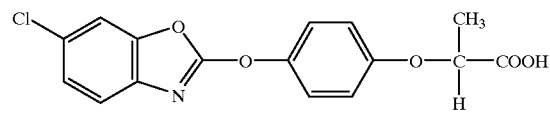

(R)-2-[4-(6 chloro-1,3-benzoxazol-2-yloxy)phenoxy] propionic acid, including, inter alia, the most common use form fenoxaprop-P-ethyl, the abovementioned compounds B1) being known from Pesticide Manual, 10th edition 1994, p. 439AA1 and 441–442, B2) isoproturon

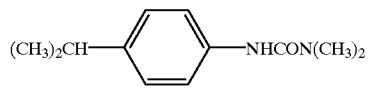

3-4-isopropylphenyl)-1,1-dimethylurea Pesticide Manual, 10th edition 1994, p. 611–612, B3) diclofop

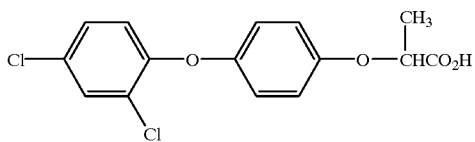

(RS)-²-[4-(2,4-dichlorophenoxy)phenoxy]propionic acid including, inter alia, as most important use form the methyl ester diclofop-methyl Pesticide Manual, 10th edition 1994, p. 315–317;

B4) clodinafop

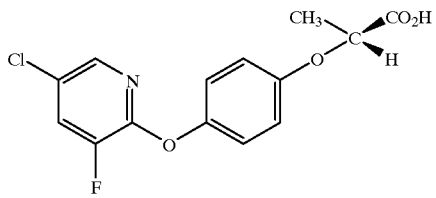

(R)-2-[4-(5-chloro-3-fluoro-2-pyridylox)phenoxy] propionic acid including in particular also the use form as clodinafop-propagyl Pesticide Manual, 10th edition 1994, p. 216–217

B5) mixtures of B4) and cloquintocet

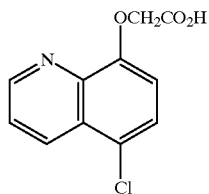

(5-chloroquinolin-8-yloxy)acetic acid, which is also employed as cloquintocet-mexyl and represents a particularly preferred safener for B4), Pesticide Manual, 10th edition 1994, p. 226–227, B6) chlortoluron

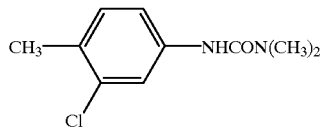

3(3-chloro-p-tolyl)-1-dimethylurea Pesticide Manual, 10th edition 1994, p. 194–196, B7) methabenzthiazuron

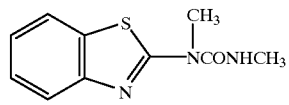

1-(1,3-benzothiazol-2-yl)-1,3-dimethylurea Pesticide Manual, 10th edition 1994, p. 670–671, B8) imazamethabenz,

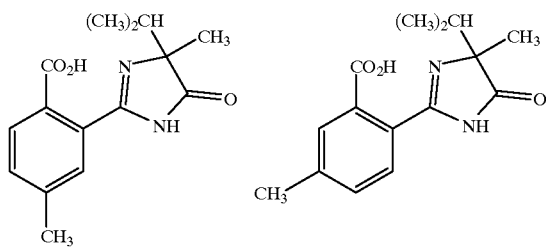

a reaction product comprising (±)-(4-isopropyl-4-ethyloxo-2-imidazolin-2-yl)-m-toluic acid and (±)-6-(4-isopropyl-4-methyl-4-oxo-2-imidazolin-2-yl)-p-toluic acid, it being in each case alternatively possible to employ the methyl esters known as imazamethabenz-methyl Pesticide Manual, 10th edition 1994, p. 582–584, B9) tralkoxydim

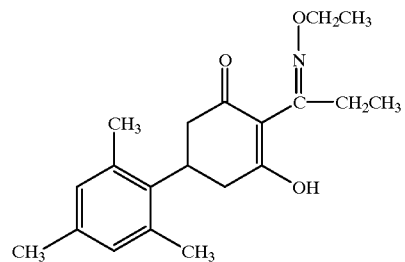

2-[1-(ethoxyimino)propyl]-3-hydroxy-5-mesitylcyclohex-2-enone Pesticide Manual, 10th edition 1994, p. 995–996

B10) difenzoquat

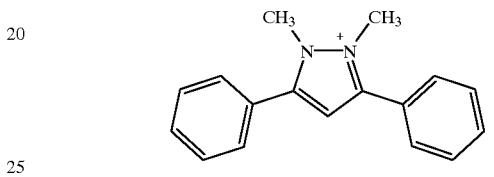

1,2-dimethyl-3,5-diphenylpyrazolium for example also as difenzoquat-metilsulfate Pesticide Manual, 10th edition 1994, p. 330–331

B11) flamprop, flamprop-M,

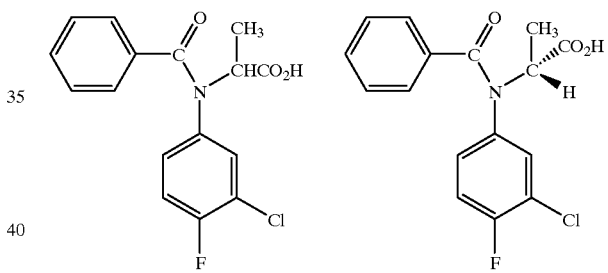

N-benzoyl-N-(3-chloro-4-fuorophenyl)-DL-alanine
N-benzoyl-N-3-chloron-A4luorophenyl)-D-alanine
including, inter alia, flamprop-methyl, flamprop-M-methyl, flamprop-M-isopropyl Pesticide Manual, 10th edition 1994, p. 464–465 and 466–468
and
B12) pendimethalin

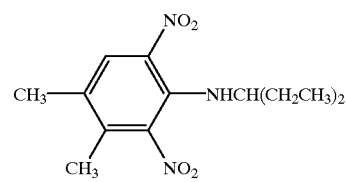

N-(1-ethylpropyl)-2,6-dinitro-3,4-xylidine Pesticide Manual, 10th edition 1994, p. 779–780.

The compounds B1) to B12) are herbicides known, for example, from the reference given for the respective compound, which have specific selective activity against grasses in cereals. In addition to the parent compound, whose formula is generally also given for reasons of clarity, reference is also made to derivatives of the parent compounds which are usually employed. Thus, for example, B4) (clodinafop) is usually employed in the form of the propargyl ester and diclofop (B3)) is employed as methyl ester, etc. When optically active forms of the type B compounds are customary, these forms are also referred to (for example fenoxaprop-ethyl and fenoxaprop-P-ethyl, etc.).

The compounds B1), B3) and B4) belong to the class of chemical substances of the 2-(4-aryloxyphenoxy)propionic acids or to the ester derivatives. B2), B6) and B7) are ureas, whereas B8) is a representative of the imidazolinones, B9) is a cyclohexanedione oxime, B11) is an arylalanine and 812) is a 2,6-dinitroaniline. Thus, although the representatives of this group have relatively differing chemical structures, they do nevertheless, owing to their activity spectrum and to the fact that they are synergists of the compounds of the formula 1, form a coherent subgroup.

Particularly advantageous mixtures in the context of the invention result when the combination according to the invention comprises the type B compounds diclofop-methyl, fenoxaprop-P-ethyl, isoproturon, mixtures of clodinafop-propargyl with cloquintocet-mexyl (known under the protected name Topik®) and/or imazamethabenz-methyl.

The invention furthermore provides compositions which comprise the herbicides of type B from subgroup Bb). Particular preference is given to employing one or more herbicides which have selective activity against dicotyledons in cereals and which are selected from the group comprising aryloxyalkylcarboxylic acids, hydroxybenzonitriles, diphenyl ethers, azoles and pyrazoles, diflufenican and bentazone.

From among the possible aryloxyalkylcarboxylic acids, preference is given in turn to those herbicides which are selected from the group comprising B13) mecoprop, mecoprop-P

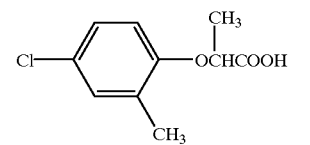

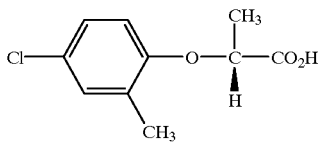

(RS)-2-(4-chloro-o-tolyloxy)propionic acid (R)-2-(4-chloro-o-tolyloxy)propionic acid Pesticide Manual, 10th edition 1994, p. 646–647 and 647–648,

B14) MCPA

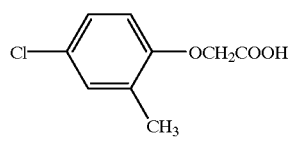

(4-chloro-2-methylphenoxy)acetic acid, the forms which are predominantly employed are, inter alia, MCPA-butotyl, MCPA-dimethylammonium, MCPA-isoctyl, MCPA-potassium, MCPA-sodium, Pesticide Manual, 10th edition 1994, p. 638–640, B15) dichlorprop, dichlorprop-P

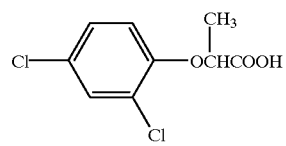

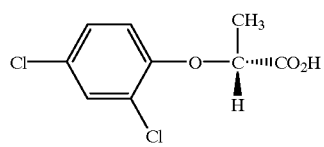

(RS)-2-(2,4dichlorophenoxy)propionic acid (R)-2-(2,4-dichlorophenoxy)propionic acid commonly used are, inter alia, also dichlorprop-butotyl, dichlorprop-ethylammonium, dichlorprop-isoctyl, dichlorprop-potassium Pesticide Manual, 10th edition 1994, p. 309–311 and 311–312,

B16) 2,4-D

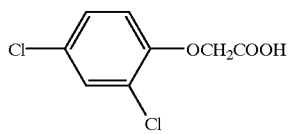

(2,4-dichlorophenoxy)acetic acid frequently used forms: 2,4-D-butotyl, 2,4-D-butyl, 2,4-D-dimethylammonium, 2,4-D-diolamine, 2,4D-:isoctyl, 2,4-D-isopropyl, 2,4-D-trolamine, Pesticide Manual, 10th edition 1994, p. 271–273, B17) dicamba

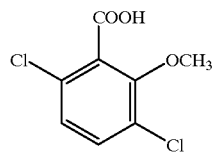

3,6-dichloro-o-anisic acid used inter alia as dicamba-dimethylammonium, dicamba-potassium, dicamba-sodium, dicamba-trolamine, Pesticide Manual, 10th edition 1994, p. 298–300 and B18) fluroxypyr

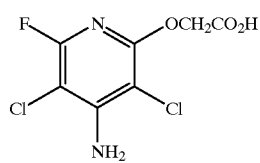

4-amino-3,5-dichloro-6-fluoro-2-pyridyloxyacetic acid, further use forms: fluoroxypyr-meptyl and particularly preferably: fluroxypyr-butoxypropylester Pesticide Manual, 10th edition 1994, p. 505–507.

Of particular interest are furthermore herbicidal compositions with hydroxybenzonitriles which have selective activity against dicotyledons in cereals. These preferably include B19) ioxynil

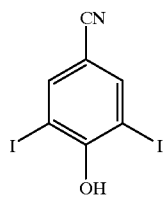

4-hydroxy-3,5-diiodobenzonitrile, common use forms: ioxynil octanoate, ioxynil-sodium, Pesticide Manual, 10th edition 1994, p. 598–600 and B20) bromoxynil

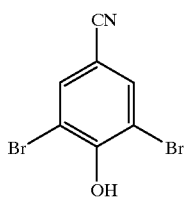

3,5-dibromo-4-hydroxybenzonitrile frequently employed as bromoxynil-octanoate, bromoxynil-potassium, Pesticide Manual, 10th edition 1994, p. 121–123.

Further advantageous compositions according to the invention comprise as herbicides of type B) one or more diphenyl ethers which have selective activity against dicotyledons in cereals and which are selected from the herbicides B21) bifenox

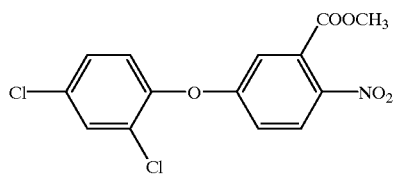

methyl 5(2,4-dichlorophenoxy)-2-nitrobenzoate Pesticide Manual, 10th edition 1994, p. 94–96, B22) fluoroglycofen

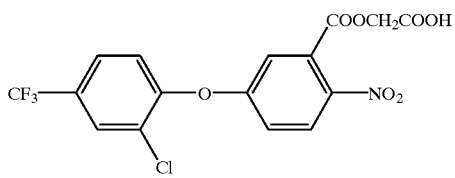

O-[5-(2-chloro-α,α,α-trifluoro-p-tolyloxy)-2-nitrobenzoyl]glycolic acid, further use form: fluoroglycofen-ethyl, Pesticide Manual, 10th edition 1994, p. 492–494, B23) lactofen

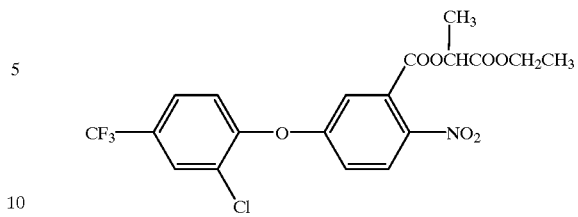

ethyl O-[5-(2chloro-α,α,α-trifluoro-p-tolyloxy)-2-nitrobenzoyl]-DL-lactate Pesticide Manual, 10th edition 1994, p. 623, B24) fomesafen

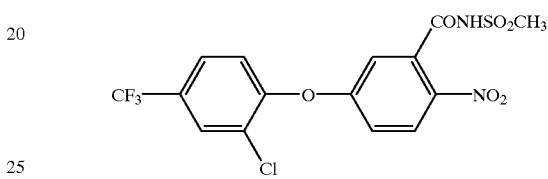

5-(2-chloro-α,α,α-trifluoro-p-tolyloxy)-N-methylsulfonyl-2-nitrobenzamide, also used as fomesafen-sodium, Pesticide Manual, 10th edition 1994, p. 520–521 and B25) oxyfluorfen

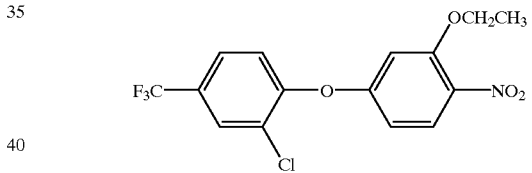

2-chloro-α,α,α-trifluoro-p-tolyl-ethoxy-4-nitrophenyl ether Pesticide Manual, 10th edition 1994, p. 764–765.

Also of particular interest are herbicidal compositions which comprise, as compound of type B, one or more azoles or pyrazoles which have selective activity against dicotyledons in cereals and which are selected from the group consisting of the herbicides

B26) ET 751

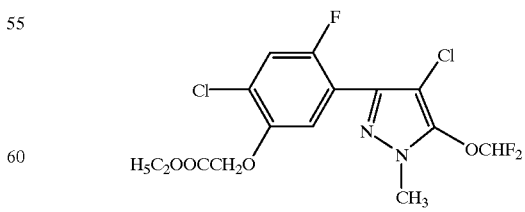

ethyl 2-chloro-5-(4-chloro-5-difluoromethoxy-1-methylpyrazol-3-yl)-4-fluorophenoxyacetate Pesticide Manual, 10th edition 1994, p. 400;

B27) azoles of the formula II

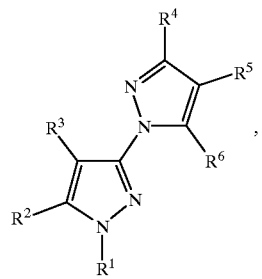

(II)

in which

R$^1$ is (C$_1$–C$_4$)-alkyl

R$^2$ is (C$_1$–C$_4$)-alkyl, (C$_1$–C$_4$)-alkylthio or (C$_1$–C$_4$)-alkoxy, each of which may be substituted by one or more halogen atoms, or R$^1$ and R$^2$ together form the group (CH$_2$)$_m$ where m=3 or 4, R$^3$ is hydrogen or halogen R$^4$ is hydrogen or (C$_1$–C$_4$)-alkyl, R$^5$ is hydrogen, nitro, cyano or one of the groups —COOR$^7$, —C(=X)NR$^7$R$^8$ or —C(=X)R$^{10}$, wherein X=O or S, R$^6$ is hydrogen, halogen, cyano, (C$_1$–C$_4$)-alkyl, (C$_1$–C$_4$)-alkylthio or —NR$^{11}$R$^{12}$, R$^7$ and R$^8$ are identical or different and each is hydrogen or (C$_1$–C$_4$)-alkyl, or R$^7$ and R$^8$ join with the nitrogen to which they are attached to form a saturated 5- or 6-membered carbocyclic ring, R$^{10}$ is hydrogen or (C$_1$–C$_4$)-alkyl, the latter optionally being substituted by one or more halogen atoms, and R$^{11}$ and R$^{12}$ are identical or different and each is hydrogen, (C$_1$–C$_4$)-alkyl or (C$_1$–C$_4$)-alkoxycarbonyl, where R$^{11}$ and R$^{12}$ may join with the nitrogen to which they are attached to form a 3-, 5- or 6-membered carbocyclic or aromatic ring in which one carbon atom may be replaced by an oxygen atom;

the azoles of the formula II being known, inter alia, from WO 94/08999; and

B28) F 8426

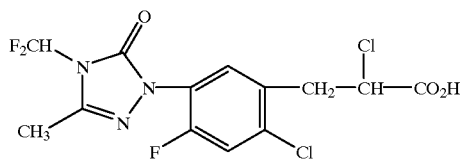

ethyl 2-chloro-3-2-chloro-4-fluoro-5-(4-difluoromethyl-4,5-dihydro-3methyl-5-oxo-1H-1,2,4-triazol-1-ylphenyl) propionate Pesticide Manual, 10th edition 1994, p. 421.

A preferred type B compound is also

B29) diflufenican

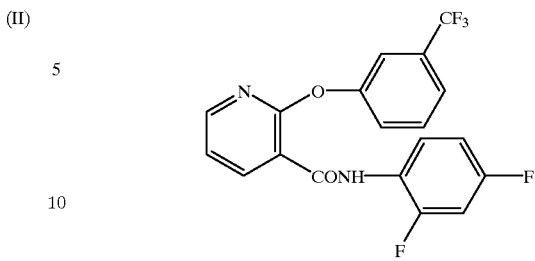

2',4'-difluoro-2-(α,α,α-trifluoro-m-tolyloxy) nicotinanilide Pesticide Manual, 10th edition 1994, p. 335–336.

A further advantageous embodiment of the invention is characterized by a herbicidal composition which comprises as herbicide of type B B30) bentazone

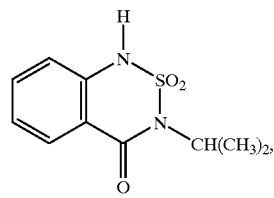

3-isopropyl-1H-2,1,3-benzothiadiazine-4(3M-one 2,2-dioxide Pesticide Manual, 10th edition 1994, p. 90–91.

From among the type B compounds having selective activity against dicotyledons in cereals {subgroup Bb)comprising the herbicidally active compounds B13) –B30) and frequently used derivatives thereof}, MCPA, mecoprop, dicamba, fluroxypyr, diflufenican, ioxynil and/or fluoroglycofen are very particularly suitable components of a herbicidal composition according to the invention.

A third subgroup of compounds, whose addition to compounds of type A makes it possible to obtain herbicidal compositions having outstanding properties, is the subgroup Bc) of the herbicides which have selective activity against grasses and dicotyledons in cereals. Type B substances having this activity profile are preferably found in the chemical substance classes of the triazine derivatives, chloroacetanilides and those sulfonylureas which differ from the sulfonylureas mentioned in formula 1. Further substance classes are, inter alia, triazoles, (thio)carbamates and furanones.

Preferred representatives include, inter alia, the herbicidally active triazine derivative B31) metribuzin

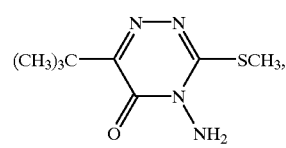

4-amino-6-tert-butyl-4,5-dihydro-3-methylthio-1,2,4-triazin-5-one Pesticide Manual, 10th edition 1994, p. 699–700.

Useful triazoles and thiocarbamates are, inter alia

B32) metosulam

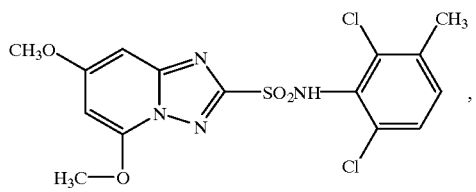

2',6'-dichloro-5,7-dimethoxy-3'-methyl[1,2,4]triazolo[1,5-α]pyrimidine-2-sulfoanilide Pesticide Manual, 10th edition 1994, p. 696–697;

B32a) flupoxam

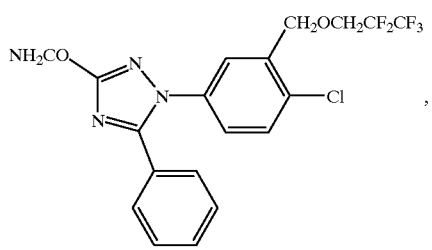

1-[4-chloro-3-(2,2,3,3,3-pentafluoropropoxymethyl)phenyl]-5-phenyl-1H-1,2,4-triazol-3-carboxamide Pesticide Manual, 10th edition 1994, p. 495–496; and/or B33) prosulfocarb

S-benzyl dipropylthiocarbamate Pesticide Manual, 10th edition 1994, p. 863–864.

Preferred representatives furthermore include the herbicidally active furanone derivative B34) flurtamone

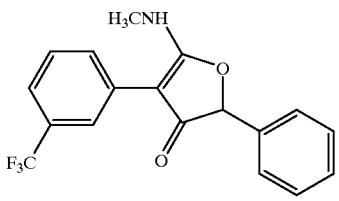

(RS)-5-methylamino-2-phenyl(α,α,α-trifluoro-m-tolyl)furan-3(2H)-one Pesticide Manual, 10th edition 1994, p. 509.

Advantageous embodiments of the herbicidal compositions according to the invention furthermore comprise, as component of type B, one or more sulfonylureas having selective activity against grasses and dicotyledons in cereals and differing from the type A compounds. Particularly preferred sulfonylureas of this kind are, inter alia B35) amidosulfuron

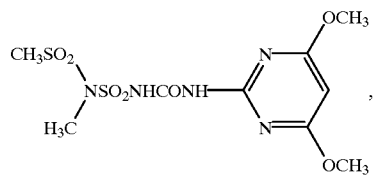

1-(4,6-dimethoxypyrimidin-2-yl)-3-mesyl(methyl)sulfamoylurea Pesticide Manual, 10th edition 1994, p. 34–35, B36) metsulfuron

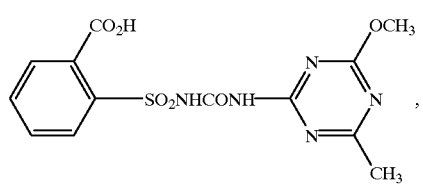

2-(4-methoxy-methyl-1,3,5-triazin-2-ylcarbamoylsulfamoyl)benzoic acid, usually employed as metsulfuron-methyl, Pesticide Manual, 10th edition 1994, p. 701–702, B37) tribenuron

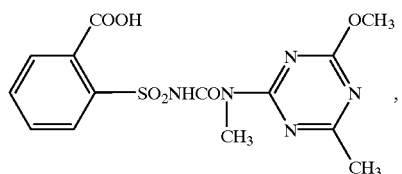

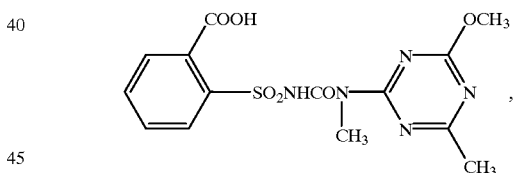

2-[4-methoxy-6-methyl-1,3,5triazin-2-yl(methyl)carbamoylsulfamoyl]benzoic acid, usually employed as tribenuron-methyl Pesticide Manual, 10th edition 1994, p. 1010–1011, B38) thifensulfuron

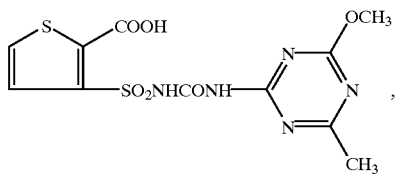

3(4-methoxysmethyl-1,3,5-triazin-2-ylcarbamoylsulfamoyl)thiophene-2-carboxylic acid, usually employed as thifensulfuron-methyl Pesticide Manual, 10th edition 1994, p. 976–978, B39) triasulfuron

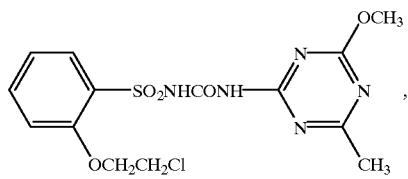

1-[2-(2chloroethoxy)phenylsulfonyl]3(4-methoxy-6-methyl-1, 3, 5-triazin-2-yl)urea Pesticide Manual, 10th edition 1994, p. 1005–1006, B40) chlorsulfuron

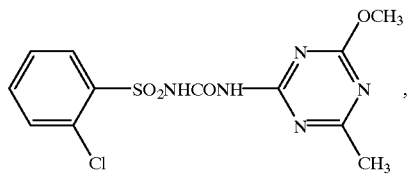

1-(2-chlorophenylsulfonyl)-3-(4-methoxy-6-methyl-1,3,5-triazin-2-yl)urea Pesticide Manual, 10th edition 1994, p. 203–205, B41) sulfonylureas of the formula III

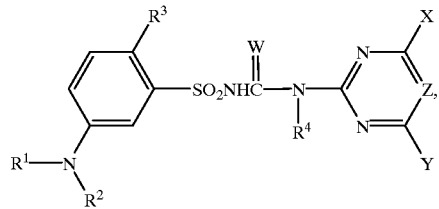

in which $R^1$ is $(C_1–C_4)$-alkyl, $(C_2–C_4)$-alkenyl or $(C_2–C_4)$-alkynyl, preferably $(C_1–C_4)$ alkyl, allyl or propargyl, $R^2$ is CO—$R^5$, COOR$^6$, CO—NR$^8$R$^9$, CS—NR$^{10}$R$^{11}$, SO$_2$R$^{14}$ or SO$_2$NR$^{15}$R$^{16}$, $R^3$ is COR$^{17}$, COOR$^{18}$, CONR$^{19}$R$^{20}$ or CO—ON=CR$^{22}$R$^{23}$, preferably COOR$^{18}$, $R^4$ is hydrogen or $(C_1–C_4)$-alkyl, preferably hydrogen or methyl, $R^5$ is hydrogen, $(C_1–C_6)$-alkyl which is unsubstituted or substituted by one or more radicals selected from the group consisting of halogen, $(C_1–C_4)$-alkoxy, $(C_1–C_4)$-alkylthio or NR$^{31}$R$^{32}$, or is $(C_3–C6)$-cycloalkyl, phenyl with or without substitution, benzyl with or without substitution or heteroaryl with or without substitution, preferably H, $(C_1–C_6)$-alkyl, $(C_1–C_4)$-haloalkyl, cyclopropyl, cyclopentyl, cyclohexyl, phenyl or heteroaryl, the last two radicals being unsubstituted or substituted by one or more radicals selected from the group consisting of $(C_1–C_4)$-alkyl, $(C_1–C_4)$-alkoxy and halogen, $R^6$ is $(C_1–C_6)$-alkyl, $(C_2–C_6)$-alkenyl, $(C_2–C_6)$-alkynyl, $(C_1–C_6)$-haloalkyl or $(C_3–C_6)$-cycloalkyl, preferably $(C_1–C_4)$alkyl, $(C_1–C_4)$-haloalkyl, allyl, propargyl or $(C_3–C_6)$-cycloalkyl, $R^7$ is $(C_1–C_4)$-alkyl, $R^8$ is hydrogen, $(C_1–C_6)$-alkyl, $(C_1–C_4)$-haloalkyl or $(C_1–C_4)$-alkoxy or $(C_1–C_4$-alkoxy)-carbonyl, $R^9$ is hydrogen, $(C_1–C_6)$-alkyl which is unsubstituted or substituted by one or more radicals selected from the group consisting of halogen, $(C_1–C_4)$-alkoxy and NR$^{31}$R$^{32}$ or is CO—R$^{33}$, CO—OR$^{34}$ or NR$^{35}$R$^{36}$ or $R^8$ and $R^9$ together form a bivalent radical of the formula —(CH$_2$)$_4$—, —(CH$_2$)$_5$— or —CH$_2$CH$_2$-O-CH$_2$CH$_2$—, $R^{10}$ is analogous to $R^8$, $R^{11}$ is analogous to $R^9$, $R^{12}$ is analogous to $R^6$, $R^{13}$ is analogous to $R^6$, $R^{14}$ is $(C_1–C_6)$alkyl, $(C_1–C_6)$haloalkyl, preferably $(C_1–C_4)$-alkyl or $(C_1–C_4)$-haloalkyl, $R^{15}$ and $R^{16}$ are independently of one another identical or different and are each hydrogen or $(C_1–C_4)$alkyl, $R^{17}$ is hydrogen, $(C_1–C_4)$-alkyl, $(C_1–C_4)$-haloalkyl, $(C_3–C_6)$-cycloalkyl, phenyl or heteroaryl, the last two radicals being unsubstituted or substituted, $R^{18}$ is hydrogen $(C_1–C_4)$-alkyl, $(C_2–C_6)$-alkenyl or $(C_2–C_6)$-alkynyl, the last three radicals being unsubstituted or substituted by one or more radicals selected from the group consisting of halogen, $(C_1–C_4)$-alkoxy, $(C_1–C_4)$-alkylthio and NR$^{31}$R$^{32}$, or is $(C_3–C_6)$-cycloalkyl or $(C_3–C_6)$-cycloalkyl-$(C_1–C_3)$-alkyl, $R^{19}$ is analogous to $R^8$, $R^{20}$ is analogous to $R^9$, $R^{22}$ and $R^{23}$ are independently of one another identical or different and are each hydrogen or $(C_1–C_2)$-alkyl, $R^{29}$ is hydrogen, hydroxyl, amino, NHCH$_3$, N(CH$_3$)$_2$, $(C_1–C_4)$-alkyl or $(C_1–C_4)$-alkoxy, $R^{30}$ is hydrogen or $(C_1–C_4)$-alkyl, $R^{31}$ and $R^{32}$ are independently of one another identical or different and are each hydrogen or $(C_1–C_4)$alkyl, $R^{33}$ is hydrogen, $(C_1–C_4)$-alkyl, $(C_1–C_4$haloalkyl, $(C_3–C_6)$-cycloalkyl or phenyl which is unsubstituted or substituted by one or more radicals selected from the group consisting of halogen, $(C_1–C_4)$-alkyl and $(C_1–C_4)$-alkoxy, $R^{34}$ is $(C_1–C_4)$-alkyl, allyl, propargyl or cycloalkyl, $R^{35}$ and $R^{36}$ are independently of one another identical or different and are each hydrogen or $(C_1–C_4)$-alkyl, W is oxygen or sulfur, X is $(C_1–C_4)$-alkyl, $(C_1–C_4)$-alkoxy, $(C_1–C_4)$-haloalkyl, $(C_1–C_4)$-alkylthio halogen or mono- or di-$C_1–C_2$-alkyl)-amino, preferably methyl, ethyl, methoxy, ethoxy, methylthio, ethylthio, chlorine, NHCH$_3$ or N(CH$_3$)$_2$, Y is $(C_1–C_4)$-alkyl, $(C_1–C_4)$-alkoxy, $(C_1–C_4)$haloalkyl or $(C_1–C_4)$-alkylthio, preferably methyl, ethyl, methoxy, ethoxy and Z is CH or N, the sulfonylureas of the formula III being known from WO 94/10154, a particularly interesting combination partner B) being compounds of the formula III in which $R^1$ is methyl, ethyl, n-propyl, isopropyl or allyl, $R^2$ is CO-$R^5$, COOR$^6$, CO—NR$^8$R$^9$, CS—NR$^{10}$R$^{11}$, SO$_2$R$^{14}$ or SO$_2$NR$^{15}$R$^{16}$, $R^3$ is COR$^{17}$, COOR$^{18}$, CONR$^{19}$R$^{20}$ or CO—ON=CR$^{22}$R$^{23}$, $R^4$ is hydrogen or $(C_1–C_4)$-alkyl, $R^5$ is hydrogen, $(C_1–C_4)$-alkyl, $(C_1–C_2)$-haloalkyl, cyclopropyl, phenyl, benzyl or heteroaryl having 5 or 6 ring atoms, the last 3 radicals being unsubstituted or substituted by one or more halogen atoms, $R^6$ is $(C_1–C_4)$-alkyl, allyl, propargyl or cyclopropyl, $R^8$ is hydrogen, $(C_1–C_4)$-alkyl, $(C_1–C_4)$-haloalkyl or $(C_1–C_4$-alkoxy)-carbonyl, $R^9$–$R^{11}$ are independently of one another identical or different H or $(C_1–C_4)$-alkyl, $R^{14}$ is $(C_1–C_4)$-alkyl, $R^{15}$ and $R^{16}$ are independently of one another identical or different hydrogen or $(C_1-C_4)$-alkyl, $R^{17}$ is hydrogen, $(C_1-C_4)$alkyl, $(C_1-C_4)$-haloalkyl, $(C_3-C_6)$-cycloalkyl, phenyl or heteroaryl, the last two radicals being unsubstituted or substituted, $R^{18}$ is hydrogen, $(C_1C_4)$-alkyl, $(C_2-C_6)$-alkenyl or $(C_2-C_6)$-alkynyl, the last three radicals being unsubstituted or substituted by one or more radicals selected from the group consisting of halogen, $(C_1-C_4)$-alkoxy, $(C_1-C_4)$-alkylthio and $NR^{31}R^{32}$, or $(C_3-C_6)$-cycloalkyl or $(C_3-C_6)$-cycloalkyl-$(C_1-C_3)$-alkyl, $R^{19}$ is analogous to $R^8$, $R^{20}$ is analogous to $R^9$, $R^{22}$ and $R^{23}$ are independently of one another identical or different hydrogen or $(C_1-C_2)$-alkyl, $R^{31}$ and $R^{32}$ are independently of one another identical or different hydrogen or $(C_1-C_4)$-alkyl, W is oxygen or sulfur, X is $(C_1-C_4)$-alkyl, $(C_1-C_4)$-alkoxy, $(C_1-C_4)$haloalkyl, $(C_1-C_4)$-alkylthio, halogen or mono- or di-$(C_1-C_2$-alkyl) amino, Y is $(C_1-C_4)$-alkyl, $(C_1-C_4)$-alkoxy, $(C_1-C_4)$haloalkyl or $(C_1-C_4)$-alkylthio, and Z is CH or N, very particularly interesting combination partners B) also being those compounds of the formula III in which $R^1$ is methyl, ethyl, n-propyl, i-propyl or allyl, $R^2$ is $CO—R^5$, $COOR^6$, $CO—NR^8R^9$, $CS—NR^{10}R^{11}$, $SO_2R^{14}$ or $SO_2NR^{15}R^{16}$, $R^5$ is hydrogen, $(C_1-C_4)$-alkyl, $(C_1-C_2)$-haloalkyl, cyclopropyl, phenyl, benzyl or heteroaryl having 5 or 6 ring atoms, the last 3 radicals being unsubstituted or substituted by one or more halogen atoms, $R^6$ is $(C_1-C_4)$-alkyl, allyl, propargyl or cyclopropyl, $R^8$ is hydrogen, $(C_1-C_4)$-alkyl, $(C_1-C_4)$-haloalkyl or $(C_1-C_4$-alkoxy)-carbonyl, $R^9-R^{11}$ are independently of one another identical or different H or $(C_1-C_4)$-alkyl, $R^{14}$ is $(C_1-C_4)$-alkyl and $R^{15}$ and $R^{16}$ are independently of one another identical or different hydrogen or $(C_1-C_4)$-alkyl, most particularly advantageous combination partners B) being those compounds of the formula III in which $R^5$ is H, $CH_3$, $C_2H_5$, n- or i-$C_3H_7$, n-, i-, t- or 2-butyl, n-pentyl, $CF_3$, $CH_2Cl$, $CCl_3$, $CH_2Br$, $CH_2CCl_3$, cyclopropyl, phenyl, thienyl, furyl or pyridyl, where the last four radicals may be substituted by 1 to 3 halogen atoms, B42) sulfonylureas of the formula IV and agriculturally tolerable and acceptable salts thereof

IV)

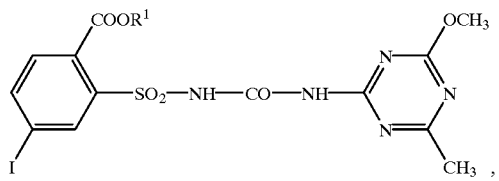

in which $R^1$ is $(C_1-C_8)$-alkyl, $(C_3-C_4)$-alkenyl, $(C_3-C_4)$-alkynyl or $(C_1-C_4)$-alkyl which is mono- to tetrasubstituted by radicals selected from the group consisting of halogen and $(C_1-C_2)$-alkoxy, where in the herbicide of the formula (IV) or the salt thereof particularly preferably $R^1$ is methyl;

and where likewise those salts have particularly favorable activity where the salt of the herbicide of the formula (IV) is formed by replacing the hydrogen of the $—O_2—NHCO—$ group by a cation selected from the group of the alkali metals, alkaline earth metals and ammonium, preferably sodium, the compounds of the formula IV being known, for example, from WO 92/13845, B43) flupyrsulfuron (DPX-KE459)

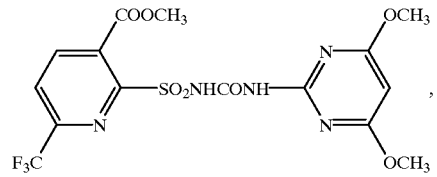

preferably as sodium salt, introduced at the Brighton Crop Protection Conference Weeds 1995, B44) MON 48500 preferably as sodium salt, introduced at the Brighton Crop Protection Conference Weeds 1995, and/or B45) sulfosulfuron (MON37500)

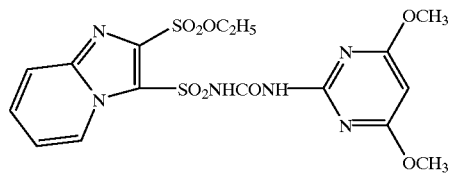

introduced at the Brighton Crop Protection Conference Weeds 1995.

From among the type B compounds having selective activity against grasses and dicotyledons in cereals {subgroup Bc) comprising the herbicidally active compounds B31)–B45) and commonly used derivatives thereof}, metsulfurone-methyl, tribenurone-methyl, sulfonylureas of the formula IV (B42)) and/or amidosulfurone are very particularly suitable components of a herbicidal composition according to the invention.

A fourth subgroup of compounds, whose addition to compounds of type A makes it possible to obtain herbicidal compositions having superadditive activity, is the subgroup Bd) of the herbicides which have activity against weed grasses and broad-leaved weeds and which are nonselective in non-crop areas and/or selective in transgenic crops. Type B substances which answer this description include, inter alia, B46) glufosinate, glufosinate-P

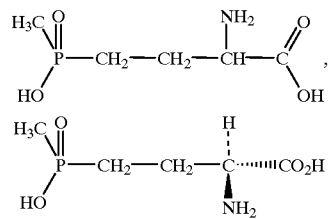

4-[hydroxy(methyl)phosphinoyl]-DL-homoalanine,

4-[hydroxy(methyl)phosphinoyl]-L-homoalanine, each of which is preferably employed as glufosinate-ammonium or glufosinate-P-ammonium, Pesticide Manual, 10th edition 1994, p. 541–542 and/or B47) Glyphosate

HO$_2$CCH$_2$NHCH$_2$P(OH)$_2$

N-(phosphonomethyl)glycine, which is preferably employed as glyphosate-isopropylammonium, glyphosate-sesquinatrium, glyphosate-trimesium, Pesticide Manual, 10th edition 1994, p. 542–544.

Combinations of the active compounds A+B show super-additive effects, i.e. with the same level of control of harmful plants, the herbicidal compositions according to the invention permit reduction of the application rate, make it possible to control some species at all and/or allow the safety margin, especially in cereal crops, to be increased. Both are advantageous, economically as well as ecologically. Here, the selection of the amounts of components A+B to be employed, the ratio of the components A: B and the application sequence as well as, for example, the formulation to be selected, depend on a large number of factors. Not insignificant in this context are, inter alia, the kind of co-components, the development stage of the weed grasses or broad-leaved weeds, the range of weeds to be controlled, environmental factors, climatic conditions, soil properties, etc.

In a very particularly preferred embodiment of the invention, herbicidal compositions according to the invention have a synergistically effective content of a combination of the compounds of the formula I or salts thereof (type A compounds) with compounds from group B. It has to be emphasized that even in combinations having application rates or weight ratios of A:B where a synergism is not in each case immediately evident—for example because the individual compounds are usually present in the combination in very different application rates or else because the control of the harmful plants by the individual compounds is already very good—the herbicidal compositions of the invention generally have an inherent synergistic activity.

The application rates of herbicide A are generally between 0.1 and 100 g of ai/ha (ai =active ingredients, i.e. the application rate based on the active compound), preferably between 2 and 40 9 of ai/ha.

The application rates of compounds of type B are usually:

| Type B compounds | Application rates g of ai/ha | |
|---|---|---|
| | standard | preferred |
| Ba) grass herbicides in cereals {e.g. B1)-B12)} | 10 to 4000 | 50 to 1000 |
| Bb) dicotyledon herbicides in cereals {e.g. B13)-B16)} | 50 to 3000 | 100 to 2000 |
| Bb) dicotyledon herbicides in cereals {e.g. B17)} | 50 to 1000 | 100 to 500 |
| Bb) dicotyledon herbicides in cereals {e.g. B18)} | 50 to 300 | 50 to 200 |
| Bb) dicotyledon herbicides in cereals {e.g. B19) and B20)} | 50 to 1000 | 100 to 500 |
| Bb) dicotyledon herbicides in cereals {e.g. B21) to B25)} | 5 to 1000 | 20 to 500 |
| Bb) dicotyledon herbicides in cereals {e.g. B26) to B28)} | 10 to 60 | 20 to 50 |
| Bb) dicotyledon herbicides in cereals {e.g. B29)} | 50 to 500 | 100 to 300 |
| Bb) dicotyledon herbicides in cereals {e.g. B30)} | 500 to 2500 | 1000 to 2000 |
| Bc) grass and dicotyledon herbicides in cereals {e.g. B31)-B34)} | 100 to 5000 | 250 to 2500 |
| Bc) grass and dicotyledon herbicides in cereals {e.g. B35)-B45)} | 2 to 80 | 5 to 50 |
| Bd) broad band herbicides which are nonselective or selective only in transgenic crops {e.g. B46) and B47)} | 100 to 3000 | 100 to 1000 |

In the combinations of the invention, the application rates of compounds of type A+compounds of type B are usually:

| Type B compounds | Application rates g of ai/ha | |
|---|---|---|
| | A + | B |
| Ba) grass herbicides in cereals {e.g. B1)-B12)} | 2 to 40 | 50 to 1000 |
| Bb) dicotyledon herbicides in cereals {e.g. B13)-B16)} | 2 to 40 | 100 to 3000 |
| Bb) dicotyledon herbicides in cereals {e.g. B17)} | 2 to 40 | 50 to 1000 |
| Bb) dicotyledon herbicides in cereals {e.g. B18)} | 2 to 40 | 50 to 2500 |
| Bb) dicotyledon herbicides in cereals {e.g. B19) and B20)} | 2 to 40 | 50 to 1000 |
| Bb) dicotyledon herbicides in cereals {e.g. B21) to B25)} | 2 to 40 | 5 to 1000 |
| Bb) dicotyledon herbicides in cereals {e.g. B26) to B28)} | 2 to 40 | 3 to 25 |
| Bb) dicotyledon herbicides in cereals {e.g. B29)} | 2 to 40 | 50 to 500 |
| Bb) dicotyledon herbicides in | 2 to 40 | 50 to 2500 |

-continued

| Type B compounds | Application rates g of ai/ha | |
|---|---|---|
| | A + | B |
| cereals {e.g. B30)} | | |
| Bc) grass and dicotyledon herbicides in cereals {e.g. B31)-B34)} | 2 to 40 | 100 to 5000 |
| Bc) grass and dicotyledon herbicides in cereals {e.g. B35)-B45)} | 2 to 40 | 2 to 80 |
| Bd) broad band herbicides which are nonselective or selective only in transgenic crops {e.g. B46) and B47)} | 2 to 40 | 100 to 3000 |

As mentioned above, both the weight ratios A:B of the combined herbicides and their application rates can vary within wide limits. In the context of the invention, preference is given to compositions which comprise compounds of the formula I or salts thereof (type A compounds) and compounds of group B in a weight ratio of 1:2500 to 20:1.

The following weight ratios are preferably employed:

| | Mixing ratio A:B | |
|---|---|---|
| Type B compounds | preferred | partic. preferred |
| Ba) grass herbicides in cereals {e.g. B1)-B12)} | 1:500 to 1:1 | 1:200 to 1:2 |
| Bb) dicotyledon herbicides in cereals {e.g. B13)-B16)} | 1:1500 to 1:1 | 1:500 to 1:10 |
| Bb) dicotyledon herbicides in cereals {e.g. B17)} | 1:500 to 1:1 | 1:300 to 1:3 |
| Bb) dicotyledon herbicides in cereals {e.g. B18)} | 1:1200 to 1:1 | 1:600 to 1:3 |
| Bb) dicotyledon herbicides in cereals {e.g. B19) and B20)} | 1:500 to 1:1 | 1:200 to 1:3 |
| Bb) dicotyledon herbicides in cereals {e.g. B21) to B25)} | 1:500 to 8:1 | 1:300 to 2:1 |
| Bb) dicotyledon herbicides in cereals {e.g. B26) to B28)} | 1:20 to 20:1 | 1:10 to 10:1 |
| Bb) dicotyledon herbicides in cereals {e.g. B29)} | 1:250 to 1:1 | 1:100 to 1:3 |
| Bb) dicotyledon herbicides in cereals {e.g. B30)} | 1:1200 to 1:1 | 1:600 to 1:3 |
| Bc) grass and dicotyledon herbicides in cereals {e.g. B31)-B34)} | 1:2500 to 1:2 | 1:2000 to 1:4 |

The active compound combinations according to the invention can be present both as mixed formulations of the components which are then applied in a customary manner diluted with water, or as tank mixes which are prepared by jointly diluting the individually formulated components with water.

The active compounds of types A and B can be formulated in various ways, depending on the prevailing biological and/or chemico-physical parameters. The following are examples of suitable formulations: wettable powders (WP), emulsifiable concentrates (EC), water-soluble powders (SP), water-soluble concentrates (SL), concentrated emulsions (BW), such as oil-in-water and water-in-oil emulsions, sprayable solutions or emulsions, capsule suspensions (CS), oil- or water-based dispersions (SC), suspoemulsions, suspension concentrates, dusts (DP), oil-miscible solutions (OL), seed-dressing products, granules (GR) in the form of microgranules, spray granules, coated granules and adsorption granules, granules for broadcasting or soil application, water-soluble granules (SG), water-dispersible granules (WG), ULV formulations, microcapsules and waxes.

Among these, water-soluble wettable powders (WP), water-dispersible granules (WG), water-emulsifiable granules (EC), suspoemulsions (SE) and oil-suspension concentrates (SC) are preferred.

These individual types of formulation are known in principle and are described, for example, in: Winnacker-Küchler, "Chemische Technologie" [Chemical Technology], Volume 7, C. Hauser Verlag Munich, 4th Ed. 1986; Wade van Valkenburg, "Pesticide Formulations", Marcel Dekker, N.Y., 1973; K. Martens, "Spray Drying Handbook", 3rd Ed. 1979, G. Goodwin Ltd. London.

The formulation auxiliaries required, such as inert materials, surfactants, solvents and other additives are also known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; Marsden, "Solvents Guide"; 2nd Ed., Interscience, N.Y. 1963; =McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesellschaft, Stuttgart 1976; Winnacker-Küchler, "Chemische Technologie" [Chemical Technology], Volume 7, C. Hauser Verlag Munich, 4th Ed. 1986.

Based on these formulations, it is also possible to prepare combinations with other pesticidally active compounds, herbicides, insecticides, fungicides, and also antidotes, safeners, fertilizers and/or growth regulators, for example in the form of a ready mix or a tank mix.

The herbicide combinations of the invention are prepared particularly advantageously by formulating the compounds of the formula I or salts thereof (type A compounds) with one or more compounds of type B similar to a conventional crop protection formulation from the group consisting of water-soluble wettable powders (WP), water-dispersible granules (WDG), water-emulsifiable granules (WEG), suspoemulsions (SE) and oil suspension concentrates (SC).

Wettable powders are preparations which are uniformly dispersible in water and which, besides the active compounds, also comprise ionic and/or nonionic surfactants (wetting agents, dispersants), for example polyethoxylated alkylphenols, polyethoxylated fatty alcohols, polyethoxylated fatty amines, fatty alcohol polyglycol ether sulfates, alkanesulfonates or alkylarylsulfonates, sodium lignosulfonate, sodium 2,2'-dinaphthylmethane-6,6'- disulfonate, sodium dibutyinaphthalene-sulfonate or else sodium oleoylmethyltaurinate, in addition to a diluent or inert substance.

Emulsifiable concentrates are prepared by dissolving the active compound or active compounds in an organic solvent, for example butanol, cyclohexanone, dimethylformamide, xylene, or else higher-boiling aromatics or hydrocarbons with the addition of one or more ionic and/or nonionic surfactants (emulsifiers). Examples of emulsifiers which can be used are: calcium salts of alkylarylsulfdnic acids, such as calcium dodecylbensulfonate, or nonionic emulsifiers such as fatty acid polyglycol esters, alkylaryl polyglycol ethers, fatty alcohol polyglycol ethers, -propylene oxide/ethylene oxide condensates (for example block copolymers), alkyl polyethers, sorbitan fatty acid esters, polyoxyethylene sorbitan fatty acid esters or other polyoxyethylene sorbitan esters.

Dusts are obtained by grinding the active compound or the active compounds with finely divided substances, for example talc, natural clays such as kaolin, bentonite and pyrophyllite, or diatomaceous earth.

Granules can be prepared either by spraying the active compound or the active compounds onto adsorptive granulated inert material or by applying active compound concentrates to the surface of carriers such as sand, kaolinites or of granulated inert material by means of binders, for example polyvinyl alcohol, sodium polyacrylate or else mineral oils.

Water-dispersible granules are generally prepared by the customary processes such as spray drying, fluidized-bed granulation, disk granulation, mixing with high-speed mixers and extrusion without solid inert material. It is also possible to granulate suitable active compounds in the manner customarily used for preparing fertilizer granules—if appropriate in a mixture with fertilizers.

Generally, the agrochemical preparations according to the invention comprise 0.1 to 99% by weight, in particular 2 to 95% by weight, of active compounds of types A and B, in addition to customary formulation auxiliaries.

The concentrations of the active compounds A+B in the formulations may vary. In wettable powders, the active compound concentration is, for example, approximately 10 to 95% by weight, the remainder to 100% by weight being composed of customary formulation components. In the case of emulsifiable concentrates, the active compound concentration may amount to approximately 1 to 85% by weight, preferably 5 to 80% by weight. Formulations in the form of dusts comprise approximately 1 to 25% by weight, in most cases 5 to 20% by weight, of active compounds, and sprayable solutions comprise approximately 0.2 to 25% by weight, preferably 2 to 20% by weight, of active compounds. The active compound content of granules such as dispersible granules depends partly on whether the active compound is in liquid or solid form and on which granulation auxiliaries and fillers are being used. In general, the content of the water-dispersible granules amounts to between 10 and 90% by weight.

In addition, the abovementioned active compound formulations comprise, if appropriate, the tackifiers, wetting agents, dispersants, emulsifiers, penetrants, preservatives, antifreeze agents, solvents, fillers, colorants, carriers, antifoams, evaporation inhibitors and pH and viscosity regulators which are customary in each case.

Owing to the relatively low application rate of the combinations of A+B according to the invention, they are generally already very well tolerated. In particular, the combinations according to the invention permit a reduction of the absolute application rate, compared with the individual application of a herbicidally active compound. However, to increase the tolerability and/or selectivity of the herbicide combinations according to the invention, if desired, even more, it is advantageous to apply these jointly in a mixture or successively at different times together with safeners or antidotes. Suitable safeners or antidotes for the combinations according to the invention are the compounds known, for example, from EP-A33 131 (ZA-89/1960), EP-A-269 806, (U.S. Pat. No. 4,891,057), EP-A-346 620 (AU-A-89/34951) and the international patent applications PCT/EP 90/01966 (WO-91/08202) and PCT/EP 90/02020 (WO-91/078474) and the literature cited therein, or they can be prepared by the methods described therein. Further suitable safeners are known from EP-A-94 349 (U.S. Pat. No. 4,902,304), EP-A-191 736 (U.S. Pat. No. 4,881,966) and EP-A0 492 366 and the literature cited therein.

In the most favorable case, the herbicidal mixtures or use combinations of the invention additionally comprise C) one or more compounds of the formulae C1 and C2,

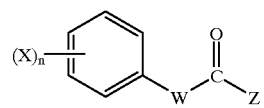

(C1)

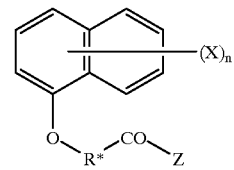

(C2)

in which

X is hydrogen, halogen, $(C_1-C_4)$alkyl, $(C_1-C_4)$-alkoxy, nitro or $(C_1-C_4)$-haloalkyl, X is $OR^1$, $SR^1$, $NR^1R$, where R is hydrogen, $(C_1-C_6)$-alkyl, $(C_1-C_6)$-alkoxy or phenyl with or without substitution, or is a saturated or unsaturated 3- to 7-membered heterocycle having at least one nitrogen atom and up to three hetero atoms which is linked to the carbonyl group via the nitrogen atom and which is unsubstituted or substituted by radicals selected from the group consisting of $(C_1-C_4)$-alkyl, $(C_1-C_4)$-alkoxy and phenyl with or without substitution, preferably a radical of the formula $OR^1$, $NHR^1$ or $N(CH_3)_2$, in particular $OR^1$, $R^*$ is a $(C_1-C_2)$-alkylene chain (=$(C_1-C_2)$-alkanediyl chain) which may additionally be substituted by one or two $(C_1-C_4)$-alkyl radicals or by $[(C_1-C_3)$-alkoxy]carbonyl, preferably —$CH_2$—, $R^1$ is hydrogen, $(C_1-C_{18})$-alkyl, $(C_3-C_{12})$-cycoalkyl, $(C_2-C_8)$-alkenyl or $(C_2-C_8)$-alkynyl, where the abovementioned carbon-containing radicals are unsubstituted or mono- or polysubstituted, preferably up to trisubstituted, by identical or different radicals selected from the group consisting of halogen, hydroxyl, $(C_1-C_8)$-alkoxy, $(C_1-C_8)$-alkylthio, $(C_2-C_8)$-alkenylthio, $(C_2-C_8)$-alkynylthio, $(C_2-C_8)$-alkenyloxy, $(C_2-C_8)$-alkynyloxy, $(C_3-C_7)$-cycloalkyl, $(C_3-C_7)$cycloalkyl, cyano, mono- and di- $(C_1-C_8)$alkylamino, carboxy, $(C_1-C_8)$-alkoxy-carbonyl, $(C_2-C_8)$-alkenyloxy-carbonyl, $(C_1-C_8)$-alkylthio-carbonyl, $(C_2-C_8)$-alkynyloxy-carbonyl, $(C_1-C_8)$-alkyl carbonyl, $(C_2-C_8)$-alkenyl-carbonyl, $(C_2-C_8)$-alkynyl-carbonyl, 1-(hydroxyimino)-$C_1-C_6$)-alkyl, 1-$[(C_1-C_4)$-alkylimino)]-$(C_1-C_4)$-alkyl, 1-[($C_1$–$C_4$)-alkoxyimino)]-($C_1$–$C_6$)-alkyl, [($C_1$–$C_8$)-alkyl-carbonylamino, ($C_2$–$C_8$)-alkenyl-carbonylamino, ($C_2$–$C_8$)-alkynyl-carbonylamino, aminocarbonyl, ($C_1$–$C_8$)-alkylaminocarbonyl, di-$C_1$–$C_6$)alkyl-aminocarbonyl, ($C_2$–$C_6$)-alkenyl-aminocarbonyl, ($C_2$–$C_6$)-alkynyl-aminocarbonyl, ($C_1$–$C_8$)-alkoxycarbonylamino, ($C_1$–$C_8$)-alkylaminocarbonylamino, ($C_1$–$C_6$)-alkylcarbonyloxy which is unsubstituted or substituted by halogen, $NO_2$, ($C_1$–$C_4$)-alkoxy or phenyl with or without substitution, ($C_2$–$C_6$)-alkenyl-carbonyloxy, ($C_2$–$C_6$)-alkynyl-mrbonyloxy, ($C_1$–$C_8$)-alkylsulfonyl, phenyl, phenyl-($C_1$–$C_6$)-alkoxy, phenyl-($C_2$–$C_6$)-alkoxy-carbonyl, phenoxy, phenoxy-($C_1$–$C_6$)-alkoxy, phenoxy-($C_1$–$C_6$)-alkoxy-carbonyl, phenylcarbonyloxy, phenylcarbonylamino, phenyl-($C_1$–$C_6$)-alkyl-carbonylamino, where the last nine radicals are unsubstituted in the phenyl ring or mono- or polysubstituted, preferably up to trisubstituted, by identical or different radicals selected from the group consisting of halogen, ($C_1$–$C_4$)-alkyl, ($C_1$–$C_4$)-alkoxy, ($C_1$–$C_4$)-haloalkyl, ($C_1$–$C_4$)-haloalkoxy and nitro, and radicals of the formulae $SiR'_3$, —O—$SiR'_3$, $R'_3Si$-($C_1$–$C_8$)-alkoxy, —CO—O—$NR'_2$, —O—N=$CR'_2$, —N=$CR'_2$, —O—$NR'_2$, $CH(OR')_2$ and —O—$(CH_2)_m$—$CH(OR'_2)_2$, where the R' in the abovementioned formulae independently of one another are each hydrogen, ($C_1$–$C_4$-alkyl, phenyl which is unsubstituted or mono- or polysubstituted, preferably up to trisubstituted, by identical or different radicals selected from the group consisting of halogen, ($C_1$–$C_4$)-alkyl, ($C_1$–$C_4$)-alkoxy, ($C_1$–$C_4$)-haloalkyl, ($C_1$–$C_4$)-haloalkoxy and nitro, or, as a pair, are a ($C_2C_6$)-alkylene chain, and m=0 to 6, and a radical of the formula R"O-CHR'" (OR)-($C_1$–$C_6$)-alkoxy, where the radicals R" independently of one another are each ($C_1$–$C_4$)-alkyl or together a ($C_{16}$)-alkylene radical and R'" is hydrogen or ($C_1$–$C_4$)-alkyl, R is hydrogen, ($C_1$–$C_6$alkyl, ($C_1$–$C_6$)-alkoxy or phenyl with or without substitution, n is an integer from 1 to 5, preferably 1 to 3, W is a bivalent heterocyclic radical having 5 ring atoms of the formulae W1 to W4

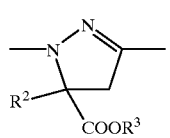
(W1)

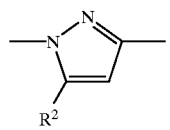
(W2)

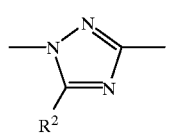
(W3)

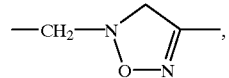
(W4)

in which $R^2$ is hydrogen, ($C_1$–$C_8$)-alkyl, ($C_1$–$C_8$)-haloalkyl, ($C_3$–$C_{12}$)-cycloalkyl or phenyl with or without substitution and $R^3$ is hydrogen, ($C_1$–$C_8$)-alkyl, ($C_1$–$C_8$)-haloalkyl, ($C_1$–$C_4$)-alkoxy-($C_1$–$C_4$)-alkyl, ($C_1$–$C_6$)-hydroxyalkyl, ($C_3$–$C_{12}$)-cycloalkyl or tri-(($C_1$–$C_4$)-alkyl)silyl, or the salts of the abovementioned compounds.

Unless specifically defined otherwise, the following definitions apply to the radicals in the formulae used in this description:

alkyl, alkenyl and alkynyl are straight-chain or branched, and have up to 8, preferably up to 4, carbon atoms;

this applies correspondingly to the aliphatic moiety of substituted alkyl, alkenyl and alkynyl radicals or radicals derived therefrom such as haloalkyl, hydroxyalkyl, alkoxycarbonyl, alkoxy, alkanoyl, haloalkoxy, etc.;

alkyl is, for example, methyl, ethyl, n-propyl, isopropyl, n-butyl, i-butyl, t-butyl and 2-butyl, pentyls, in particular n-pentyl and neo-pentyl, hexyls such as n-hexyl and i-hexyl and 1,3-dimethylbutyl, heptyls such as n-heptyl, 1-methylhexyl and 1,4-dimethylpentyl, alkenyl is, for example, inter alia allyl, 1-methylprop-2-en-1-yl, but-2-en-1-yl, but-3-en-1-yl, 1-methylbut-3-ene and 1-methylbut-2ene; alkynyl is, inter alia, propargyl, but-2-in-1-yl, but-in-1-yl, 1-methylbut-3-ine;

cycloalkyl preferably has 3 to 8 carbon atoms and is, for example, cyclobutyl, cyclopentyl, cyclohexyl or cycloheptyl. Cycloalkyl may carry up to two ($C_1$–$C_4$)-alkyl radicals as substituents.

Halogen is fluorine, chlorine, bromine or iodine, preferably fluorine, chlorine or bromine, in particular fluorine or chlorine; haloalkyl, -alkenyl and -alkynyl are alkyl, alkenyl and alkynyl, respectively, which are mono-, di- or polysubstituted by halogen, for example $CF_3$, $CHF_2$, $CH_2F$, $CF_3CF_2$, $CH_2FCHCl$, $CCl_3$, $CHCl_2$, $CH_2CH_2Cl$; haloalkoxy is, for example, inter alia $OCF_3$, $OCHF_2$, $OCH_2F$, $CF_3CF_2O$, $CF_3CH_2O$;

aryl preferably has 6 to 12 carbon atoms and is, for example, phenyl, naphthyl or biphenyl, preferably phenyl. This applies correspondingly to radicals derived therefrom such as aryloxy, aroyl or aroylalkyl;

phenyl with or without substitution is, for example, phenyl which is unsubstituted or mono- or polysubstituted, preferably mono-, di- or trisubstituted, by identical or different radicals selected from the group consisting of halogen, ($C_1$–$C_4$)alkyl, ($C_1$–$C_4$)-alkoxy, ($C_1$–$C_4$)-haloalkyl, ($C_1$–$C_4$)-haloalkoxy, ($C_1$–$C_4$)-alkylthio, ($C_2$–$C_5$)-alkoxycarbonyl, ($C_2$–$C_5$)-alkylcarbonyloxy, carbonamide, ($C_2$–$C_5$)-alkylcarbonylamino, di[($C_1$–$C_4$)-alkyl]aminocarbonyl and nitro, for example o-, m- and p-tolyl, dimethylphenyls, 2-, 3 and 4-chlorophenyl, 2-, 3 and 4-trifluoro- and -trichlorophenyl, 2,4-, 3,S, 2,5 and 2,3-dichlorophenyl or o-, m- and p-methoxyphenyl. This applies correspondingly to aryl with or without substitution.

Of particular interest are herbicidal compositions according to the invention where in the compounds of the formula C1 and C2

$R^1$ is hydrogen, ($C_1$–$C_8$)-alkyl, ($C_3$–$C_7$)-cycloalkyl, ($C_2$–$C_8$)-alkenyl or ($C_2$–$C_8$)-alkynyl, where the abovementioned carbon-containing radicals are unsubstituted or mono- or polysubstituted by halogen or mono- or disubstituted, preferably monosubstituted, radicals selected from the group consisting of hydroxyl, $(C_1–C_4)$-alkoxy, $(C_1–C_4)$-alkylthio, $(C_2–C_4)$-alkenyloxy, $(C_2–C_6)$-alkynyloxy, mono- and di- $((C_1–C_2)$-alkyl)amino, $(C_1–C_4)$-alkoxy-carbonyl, $(C_2–C_4)$-alkenyloxycarbonyl, $(C_1–C_4)$-alkynyloxy-carbonyl, $(C_2–C_4)$alkyl-carbonyl, $(C_2–C_4)$-alkenyl-carbonyl, $(C_2–C_4)$-alkynyl-carbonyl, $(C_1–C_4)$-alkylsulfonyl, phenyl, phenyl-$(C_1–C_4)$-alkoxy-carbonyl, phenoxy, phenoxy-$C_1–C_4)$-alkoxy, phenoxy-$(C_1–C_4)$-alkoxy-carbonyl, where the last six radicals are unsubstituted in the phenyl ring or mono- or polysubstituted by radicals selected from the group consisting of halogen, $(C_1–C_2)$-alkyl, $(C_1–C_2)$-alkoxy, $(C_1–C_2)$-haloalkyl, $(C_1–C_2)$-haloalkoxy and nitro, and radicals of the formulae $SiR'_3$, —O—N=$CR'_2$, —N=$CR'_2$ and —O—$NR'_2$—$CH(OR')_2$, where the R' in the abovementioned formulae independently of one another are each halogen, $(C_1–C_2)$alkyl, phenyl which is unsubstituted or mono- or polysubstituted by radicals selected from the group consisting of halogen, $(C_1–C_2)$-alkyl, $(C_1–C_2)$-alkoxy, $(C_1–C_2)$-haloalkyl, $(C_1–C_2)$-haloalkoxy and nitro, or as a pair are a $(C_4–C_5)$-alkanediyl chain, $R^2$ is hydrogen, $(C_1–C_8$-alkyl, $(C_1–C_6)$-haloalkyl, $(C_3–C_7)$-cycloalkyl or phenyl and $R^3$ is hydrogen, $(C_1–C_8)$alkyl, $(C_1–C_8)$-haloalkyl, $((C_1–C_4)$-alkoxy)-$C_1–C_4)$-alkyl, $(C_1–C6)$-hydroxyalkyl, $(C_3–C_7)$-cycloalkyl or tri-$(C_1–C_4)$-alkyl)silyl.

Also of particular interest are herbicidal compositions according to the invention where in the compounds of the formulae C1 and C2

X is hydrogen, halogen, methyl, elthyl, methoxy, ethoxy, $(C_1–C_2)$-haloalkyl, preferably hydrogen, halogen or $(C_1–C_2)$-haloalkyl.

Preference is given to herbicidal compositions according to the invention where in the compounds of the formula C1

X is hydrogen, halogen, nitro or $(C_1–C_4)$-haloalkyl,

Z is a radical of the formula $OR^1$, n is an integer from 1 to 3, $R^1$ is hydrogen, $(C_1–C8)$alkyl, $(C_3–C_7)$-cycloalkyl, where the abovementioned carbon-containing radicals are unsubstituted or mono- or polysubstituted by radicals from the group consisting of halogen or mono- or disubstituted, preferably unsubstituted or monosubstituted by radicals selected from the group consisting of hydroxyl, $(C_1–C_4)$-alkoxy, $((C_1–C_4$-alkoxy)carbonyl, $(C_2–C_6)$-alkenyloxy-carbonyl, $((C_2–C_6)$-alkynyloxy) carbonyl and radicals of the formulae $SiR'_3$, —O—N=$CR'_2$, —N=$CR'_2$, —O—N $R'_2$, where the radicals R' in the abovementioned formulae independently of one another are each hydrogen or $(C_1–C_4)$-alkyl or as a pair are a $(C_4–C_5)$-alkylene chain, $R^2$ is hydrogen, $(C_1–C_8)$-alkyl, $(C_1–C_6)$haloalkyl, $(C_3–C_7)$-cycloalkyl or phenyl and $R^3$ is hydrogen, $(C_1–C_8)$-alkyl, $(C_1–C_8)$-haloalkyl, $((C_1–C_4)$-alkoxy)$C_1–C_4)$-alkyl, $(C_1–C_6)$-hydroxyalkyl, $(C_3–C_7)$-cycloalkyl or tri-$(C_1–C_4)$-alkyl)silyl.

Preference is also given to herbicidal compositions according to the invention where in the compounds of the formula C2

X is hydrogen, halogen, or $(C_1–C_4)$-haloalkyl and n is an integer from 1 to 3, preferably $(X)_n$=5Cl, Z is a radical of the formula $OR^1$, R* is $CH_2$ and $R^1$ is hydrogen, $(C_1–C_8)$-alkyl, $(C_1–C_8)$-haloalkyl, $((C_1–C_4)$-alkoxy)-$(C_1–C_4)$-alkyl or $((C_1–C_4)$-alkenyloxy)-$(C_1–C_4)$-alkyl, preferably $(C_1–C_8)$-alkyl.

Particular preference is given to herbicidal compositions according to the invention comprising compounds of the formula C1 in which W is W1

X is hydrogen, halogen or $(C_1–C_2)$-haloalkyl and n=1–3, in particular $(X)_n$=2,4Cl$_2$, Z is a radical of the formula $OR^1$, $R^1$ is hydrogen, $(C_1–C_8)$-alkyl, $(C_1–C_4)$-haloalkyl, $(C_1–C_4)$-hydroxyalkyl, $(C_3–C_7)$-cycloalkyl, $((C_1–C_4)$-alkoxy)-$(C_1–C_4)$-alkyl, tri-$((C_1–C_2)$-alkyl)silyl, preferably $(C_1–C_4)$-alkyl, $R^2$ is hydrogen, $(C_1–C_8)$-alkyl, $(C_1–C_4)$-haloalkyl or $(C_3–C_7)$-cycloalkyl, preferably hydrogen or $(C_1–C_4)$-alkyl and $R^3$ is hydrogen, $(C_1–C_8)$-alkyl, $(C_1–C_4)$-haloalkyl, $(C_1–C_4)$-hydroxyalkyl, $(C_3–C_7)$-cycloalkyl, $((C_1–C_4)$-alkoxy)-$(C_1–C_4)$-alkyl or tri-$((C_1–C_2)$-alkyl)silyl, preferably H or $(C_1–C_4)$-alkyl.

Particular preference is also given to herbicidal compositions according to the invention comprising compounds of the formula C1 in which W is W2

X is hydrogen, halogen or $(C_1–C_2)$-haloalkyl and n=1–3, in particular $(X)_n$=2,4Cl$_2$, Z is a radical of the formula $OR^1$, $R^1$ is hydrogen, $(C_1–C_8)$-alkyl, $(C_1–C_4)$-haloalkyl, $(C_1–C_4)$-hydroxyalkyl, $(C_3–C_7)$-cyloalkyl, $((C_1–C_4)$-alkoxy)-$(C_1–C_4)$-alkyl, tri-$((C_1–C_2)$-alkyl)silyl, preferably $(C_1–C_4)$-alkyl, and $R^2$ is hydrogen, $(C_1–C_8)$-alkyl, $(C_1–C_4)$-haloalkyl, $(C_3–C_7)$-cycloalkyl or phenyl, preferably hydrogen or $(C_1–C_4)$ alkyl.

Particular preference is also given to herbicidal compositions according to the invention comprising compounds of the formula Cl in which W is W3

X is hydrogen, halogen or $(C_1–C_2)$haloalkyl and n=1–3, in particular $(X)_n$=2,4-Cl$_2$, Z is a radical of the formula $OR^1$, $R^1$ is hydrogen, $(C_1–C_8)$-alkyl, $(C_1–C_4)$-haloalkyl, $(C_1–C_4)$-hydroxyalkyl, $(C_3–C_7)$-cycloalkyl, $((C_1–C_4)$-alkoxy) $(C_1–C_4)$-alkyl, tri-$((C_1–C_2)$-alkyl)silyl, preferably $(C_1–C_4)$-alkyl, and $R^2$ is $(C_1–C_8)$-alkyl or $(C_1–C_4)$-haloalkyl, preferably $C_1$-haloalkyl.

Particular preference is also given to herbicidal compositions according to the invention comprising compounds of the formula C1 in which W is W4

X is hydrogen, halogen, nitro, $(C_1–C_4)$-alkyl, $(C_1–C_4)$-alkoxy or $(C_1–C_2)$-haloalkyl and n=1–3, preferably $CF_3$ or $(C_1–C_4)$-alkoxy, Z is a radical of the formula $OR^1$ and $R^1$ is hydrogen, $(C_1–C_4)$-alkyl or $((C_1–C_4)$-alkoxy)-carbonyl-$((C_1–C_4)$-alkyl, preferably $((C_1–C_4)$-alkoxy)-CO—$CH_2$—, $((C_1–C_4)$-alkoxy)-CO—C($CH_3$)H—, HO—CO—$CH_2$— or HO—CO—C($CH_3$)H—.

The compounds of the formula C1 are known from EP-A-0 333 131, EP-A-0 269 806, EP-A-0 346 620, International Patent Application PCT/EP 90/01966 and International Patent Application PCTIEP 90/02020 and the literature cited therein, or they can be prepared by or similar to the methods described therein. The compounds of the formula C2 are known from EP-A0 086 750, EP-A0 094 349 and EP-A-0 191 736 and the literature cited therein, or they can be prepared by or similar to the methods described therein. Furthermore, they are proposed in DE-A-40 41 121.4.

Particularly preferred antidotes or safeners or groups of compounds which have proved themselves suitable as safeners or antidotes for the product combinations of the invention described above are, inter alia:

a) Compounds of the type of the dichlorophenylpyrazolin-3-carboxylic acid (i.e. the formula C1 where W=W1 and $(X)_n$=2,4Cl$_2$), preferably compounds such as ethyl 1-(2, 4dichlorophenyl)-5(ethoxycarbonyl)-5-methyl-2-pyrazolin-3-carboxylate (compound C1—1) and related compounds as described in the International Application WO 91/07874 (PCT/EP 90/02020);

b) Derivatives of dichlorophenylpyrazolecarboxylic acid (i.e. the formula C1 where W=W2 and $(X)_n$=2,4-Cl$_2$), preferably compounds such as ethyl 1-(2,4-dichlorophenyl)-5-methylpyrazole-3-carboxylate (compound C1–2), ethyl 1-(2,4-dichlorophenyl)-5-isopropylpyrazol-3-carboxylate (compound C1–3), ethyl 1-(2,4-dichlorophenyl)-5-(1,1-dimethylethyl)pyrazole-3-carboxylate (compound C1–4), ethyl 1-(2, 4dichlorophenyl)-5-phenylpyrazole-3-carboxylate (compound C1–5) and related compounds as described in EP-A0 333 131 and EP-A40 269 806;

c) Compounds of the type of the triazolecarboxylic acids (i.e. the formula C1 where W=W3 and $(X)_n$=2,4-Cl$_2$), preferably compounds such as ethyl 1-(2,4-dichlorophenyl)-5-(trichloromethyl-1H)-1,2,4-triazole-3-carboxylate (compound C1–6, fenchlorazole) and related compounds (see EP-A0 174 562 and EP-A-0 436 620);

d) Compounds of the type of the dichlorobenzyl-2-isoxazolin-3-carboxylic acid, (i.e. the formula C1 where W=W4 and $(X)_n$=2,4-Cl$_2$), compounds of the type of the 5-benzyl- or 5-phenyl-2-isoxazolin-3-carboxylic acid, preferably compounds such as ethyl 5-(2, 4dichlorobenzyl)-2-isoxazolin-3-carboxylate (compound C1–7) or ethyl 5-phenyl-2-isoxazolin-3-carboxylate (compound (C1–8) and related compounds as described in the International Patent Application WO 91/08202 (PCT/EP 90/01966);

e) Compounds of the type of the 8-quinolinoxyacetic acid (i.e. of the formula C2 where $(X)_n$=5-Cl, hydrogen, Z=OR$^1$, R*=CH$_2$) preferably compounds such as 1-methylhex-1-yl (5-chloro-8-quinolinoxy)acetate (C2–1), 1,3-dimethylbut-1-yl (5-chloro[]quinolinoxy)acetate (C2—2), 4-allyloxybutyl (5-chloro-8-quinolinoxy)acetate (C2—3), 1-allyloxyprop-2-yl (5-chloro-8-quinolinoxy)acetate (C2–4), ethyl (5-chloro-8-quinolinoxy)acetate (C2–5), methyl (5-chloro-8-quinolinoxy)acetate (C2–6), allyl (5-chloro-8-quinolinoxy)acetate (C2–7), 2-(2-propylideneiminoxy)-1-ethyl 5-chloro-8-quinolinoxy)acetate (C2–8), 2-oxoprop-1-yl (5-chloro-8-quinolinoxy)acetate (C2–9) and related compounds as described in EP-A0 086 750, EP-A-0 094 349; and EP-A-0 191 736 or EP-A-0 492 366;

f) Compounds of the type of the (5-chloro-8-quinolinoxy) malonic acid, i.e. the formula C2 where $(X)_n$=5Cl, hydrogen, Z=OR$^1$, R*=—CH(COO-alkyl)-, preferably compounds such as diethyl (5-chloro-8-quinolinoxy) malonate, diallyl (5chloro-8-quinolinoxy)malonate, methyl ethyl (5-chloro- 8-quinolinoxy)malonate and related compounds as described and proposed in the German Patent Application P 40 41 121.4;

g) and active compounds of the type of the phenoxyacetic or phenoxypropionic acid derivatives or of the aromatic carboxylic acids such as, for example, 2,4-dichlorophenoxyacetic acid(ester) (2,4-D), 4chloro-2-methylphenoxypropionic ester (mecoprop), MCPA or 3,6-dichloro-2-methoxybenzoic acid(ester) (dicamba).

At least some of the compounds mentioned are additionally described in EP-A0 640 587, to which reference is made herewith for purposes of disclosure.

The safeners (antidotes) of the above groups a) to g) (in particular compounds of the formulae C1 and C2) reduce or neutralize phytotoxic effects which can occur when using the product combinations according to the invention in crops of useful plants, without adversely affecting the activity of the herbicides against harmful plants. Thus, it is possible to increase the area of use of the herbicide mixtures according to the invention considerably. In particular, the use of safeners permits the use of combinations which hitherto could be used only with limitations or without sufficient success, i.e. of combinations which, without safener, at low application rates with a narrow spectrum of activity did not provide sufficient control of the harmful plants.

The herbicidal mixtures according to the invention and said safeners can be applied together (in the form of a finished formulation or by the tank mix method) or in any desired sequence one after the other. The weight ratio safener: herbicide (group A, i.e. compounds of the formula 1) can vary within wide limits and is preferably in the range from 1:10 to 10:1, in particular from 1:10 to 5:1. The amounts of herbicides (type A and type B compounds) and safener which are optimal in each case depend on the type of herbicide mixture used and/or on the safener used and on the nature of the plant stand to be treated and can be determined in each individual case by suitable preliminary trials.

Depending on their properties, the safeners of type C) can be used for pretreating the seed of the crop plant (seed dressing) or be incorporated into the seed furrows before seeding or used together with the herbicide mixture before or after the plants have emerged. Preemergence treatment includes treatment of the area under cultivation before seeding and also treatment of those areas under cultivation which have been seeded but where growth has not yet taken place. Application together with the herbicide mixture is preferred. Tank mixes or finish formulations can be used for this purpose.

The required application rates of safeners can vary within wide limits, depending on the indication and the herbicide used, and are generally in the range from 0.001 to 1 kg, preferably 0.005 to 0.2 kg, of active compound per hectare.

For use, the formulations, which are in commercially available form, are, if appropriate, diluted in the customary manner, for example using water in the case of wettable powders, emulsifiable concentrates, dispersions and water-dispersible granules. Preparations in the form of dusts, granules for soil application or for broadcasting and sprayable solutions are usually not diluted further with additional inert substances prior to use.

The invention also relates to a method for controlling undesirable plants which comprises applying a herbicidally effective amount of a combination of active compounds A+B according to the invention to these plants or to the area under cultivation. The active compounds can be applied to the plants, to parts of plants, plant seeds or to the area under cultivation. In a preferred variant of the method, the compounds of the formula (i) or salts thereof (type A compounds) are applied at application rates of from 0.1 to 100 g of ai/ha, preferably from 2 to 40 g of ai/ha, while the application rates for the compounds of type B are from 1 to 5000 g of ai/ha. Preference is given to applying the active compounds of types A and B simultaneously or at different times at a weight ratio of 1:2500 to 20:1. Furthermore, particular preference is given to the joint application of the active compounds in the form of tank mixes, the optimally formulated concentrated formulations of the individual active compounds being mixed together in the tank with water and the resulting spray liquor being applied.

Since the combinations according to the invention provide extremely good crop safety and at the same time very efficient control of harmful plants, they can be considered to be selective. In a preferred variation of the method, herbicidal compositions comprising the active compound combinations according to the invention are therefore employed for selective control of undesirable plants.

The method for the selective control of harmful plants using the combination partners of type B) from subgroups Ba) to Bc) is particularly advantageous when the herbicidal compositions of the invention are employed in crops of useful cereal plants, in plantations and on meadows or pasture land. However, the use in maize or other crops of useful plants such as, for example, rice, is not precluded a priori.

The combination partners of type A, applied on their own by the pre-emergence and post-emergence method in cereals, on non-crop areas and in plantations, already control a relatively wide range of annual and perennial broad-leaved weeds, weed grasses and Cyperaceae.

Combination with the type B partners mentioned in the invention improve the activity spectrum of the type A compounds even further.

Thus, the compounds B1) to B12) complement and enhance, inter alia, the activity in the control of grass weeds in cereals and, to some extent, also the activity against broad-leaved weeds in cereals, in each case both by the pre-emergence and by the post-emergence method.

The growth-regulating herbicides from the subgroup Bb) (compounds B13) to B16)), i.e. in particular the derivatives of dichlorophenoxyacetic acid, dichlorophenoxypropionic acid, chloromethylphenoxyacetic acid and chloromethylphenoxypropionic acid and the analogous dicamba (B17)) and fluroxypyr (B18)), which is also related, serve, in the context of the invention, primarily for the more efficient control of annual and perennial broad-leaved weeds, in particular by the post-emergence method in cereals.

The compounds B19) and B20) (HBNs or bipyridilium derivatives) are herbicidally active compounds which, above all, improve the effectiveness of weed control in cereals. They are mainly employed by the post-emergence method. The nitrodiphenyl ethers B21) to B25) are employed both pre-emergence and post-emergence. They serve to enhance the activity in cereals.

The azoles and pyrazoles of the subgroup Bb) (for example B26) to B28)) can be employed particularly advantageously at comparatively low application rates by the post-emergence method for the control of dicotyledonous weeds in cereals.

B29) improves the activity spectrum of the combinations according to the invention used pre- and post-emergence in the control of weeds in cereals and other crop types, whereas B30) is a herbicidally active compound which is employed in a large number of agricultural crop plants by the post-emergence method for controlling weeds.

The triazines, triazoles, (thio)carbamates and furanones of the subgroup Bc) (for example B31) to B34)) are common active compounds which can be employed both by the pre-emergence and by the post-emergence method to increase the activity of the type A compounds in the control of weed grasses and broad-leaved weeds in cereals, in non-crop areas or in plantations.

Finally, the compounds B35) to B45) (subgroup Bc)) preferably serve in the invention for controlling broad-leaved weeds—to some extent also weed grasses—in cereals and in potatoes, in meadows or in non-crop areas, and, if appropriate, in plantations or perennial crops, by the post-emergence method, though in some instances also by the pre-emergence method.

Depending on the nature of the combination partner B, the herbicidal combinations according to the invention can also be used advantageously for controlling undesirable plants in non-crop a nd/or in transgenic crops, for example maize, rice, soya, cereals, inter alia. Particularly suitable for this purpose are the partners from group Bd) (compounds B46) and B47)).

Here, the term non-crop area does not only include paths, open spaces, industrial terrain and railways which regularly have to be kept free from weeds, but, in the context of the invention, plantation crops are also included in this generic term, even if they are not mentioned separately. Thus, the combinations according to the invention (especially those comprising combination partners from subgroup Bd)) which cover a wide spectrum of weeds extending from annual and perennial broad-leaved weeds such as, for example, Agropyron, Paspalum, Cynodon, Imperata over Pennisetum, Convolvulus and Cirsium to Rumex and others, can be employed for the selective control of harmful plants in plantation crops such as oil palm, coconut palm, rubber tree (Hevea brasiliensis), citrus, pineapples, cotton, sugar cane, coffee, cocoa and the like, and also in fruit production and viticulture. Equally, the combinations according to the invention can be employed in arable crop production using the no-till or zero-till methods. Alternatively, as already mentioned they can be used in proper non-crop areas, i.e. nonselectively on paths, in open spaces, etc. to keep these areas free of undesirable vegetation. However, the combination partners of group Bd), which are nonselective per se, do not only become selective herbicides when the crop plants have the appropriate resistance, but combinations according to the invention are also selective when used in transgenic crops. Transgenic crops are tho se in which the plants are made resistant to nonselective herbicides by genetic manipulation or selection. Crop plants which have been modified in such a way, for example maize, cereals or soya, then permit the selective use of combinations comprising B46) and/or B47).

In summary, it may be stated that superadditive (=synergistic) effects are achieved when N-[(4,6-dimethoxypyrimidin-2-yl)aminocarbonyl]-5-methylsulfonamidomethyl-2-alkoxycarbonylbenzenesulfonamides, and/or salts thereof are used together with one or more active compounds of group B, optionally and particularly preferably additionally with one or more safeners of group C. The activity in the combination s is more pronounced than that of the individual products used employed alone. These effects permit the application rate to be reduced, a broader spectrum of broad-leaved weeds and weed grasses to be controlled, a more rapid and safer action, a more prolonged action, complete control of harmful plants with only one or few applications and a widening of the period of time when the active compounds in the combination can be applied.

The abovementioned properties are required in weed control practice to keep agricultural crops free from undesirable competing plants and thus to ensure and/or increase yields from a qualitative and quantitative point of view. The combinations according to the invention markedly surpass the prior art with a view to the above-described properties.

Additionally, the combinations according to the invention permit the outstanding control of otherwise resistant harmful plants.

The following examples serve to illustrate the invention:
1. Formulation examples
a) A dust is obtained by mixing 10 parts by weight of an active compound combination according to the invention and 90 parts by weight of talc as inert substance and comminuting the mixture in a hammer mill.
b) A wettable powder which is readily dispersible in water is obtained by mixing 25 parts by weight of active compounds A+B, 64 parts by weight of kaolin-containing quartz as inert substance, 10 parts by weight of potassium ligninsulfonate and 1 part by weight of sodium oleoylmethyltaurate as wetting agent and dispersant, and grinding the mixture in a pinned-disk mill.
c) A dispersion concentrate which is readily dispersible in water is obtained by mixing 20 parts by weight of active compounds A+B with 6 parts by weight of alkylphenol polyglycol ether (®Triton X 207), 3 parts by weight of isotridecanol polyglycol ether (8 EO) and 71 parts by weight of paraffinic mineral oil (boiling range for example approximately 255 to 277° C.), and grinding the mixture in a ball mill to a fineness of below 5 microns.
d) An emulsifiable concentrate is obtained from 15 parts by weight of cyclohexanone as solvent and 10 parts by weight of ethoxylated nonylphenol as emulsifier.
e) Water-dispersible granules are obtained by mixing 75 parts by weight of active compounds A+B, 10 parts by weight of calcium lignosulfonate, 5 parts by weight of sodium lauryl sulfate, 3 parts by weight of polyvinyl alcohol and 7 parts by weight of kaolin, grinding the mixture in a pinned-disk mill and granulating the powder in a fluidized bed by spraying on water as granulation liquid.
f) Water-ispersible granules are also obtained by homogenizing, in a colloid mill, 25 parts by weight of active compounds A+B, 5 parts by weight of sodium 2,2'-dinaphthylmethane-6,6'-disulfonate, 2 parts by weight of sodium oleoylmethyltaurate, 1 part by weight of polyvinyl alcohol, 17 parts by weight of calcium carbonate and 50 parts by weight of water, precomminuting the mixture, subsequently grinding it in a bead mill and atomizing and drying the resulting suspension in a spray tower by means of a single-substance nozzle.
g) Extruder granules are obtained by mixing and grinding 20 parts by weight of active compounds A+B, 3 parts by weight of sodium lignosulfonate, 1 part by weight of carboxymethylcellulose and 76 parts by weight of kaolin and moistening the mixture with water. This mixture is extruded and subsequently dried in a stream of air.
2. Biological examples The examples mentioned below were carried out in the greenhouse, and in some instances, in field trials.

Field trials

After the natural emergence of the weeds in the cereals, the herbicides or the combinations were applied using plot sprayers. After the application, the effects, such as damage to the crop plants and the effect on broad-leaved weeds/weed grasses, were assessed by visual scoring. The herbicidal activity was assessed qualitatively and quantitatively (0–100%) by comparing untreated and treated plots with respect to the influence on plant growth and chlorotic and necrotic effects up to the total eradication of the weeds. Application was carried out at the 2–4 leaf stage of the crop plants and weeds. Evaluation was carried out approximately 4 weeks after the application.

Greenhouse trials

In the greenhouse trials, the crop plants and broad-leaved weeds/weed grasses were grown in size 13 pots and treated at the 2–4 leaf stage. The pots were subsequently stood in the greenhouse under good conditions for growth (temperature, air humidity, water supply).

Evaluation was carried out similar to the field trials, i.e. by visually scoring the treated plants in comparison to untreated control variants. These evaluations were carried out 3 weeks after the application of the preparations to be tested and combinations thereof. The experiments were carried out in duplicate.

Evaluation of the combination effects in the examples

For the assessment of the combination effects, the activity of the individual components was added and compared to the effect of mixtures of the same dosage. In many cases, it became evident that the combinations had higher efficacies than the sum of the individual effects.

In cases of less pronounced effects, the expected value was calculated using COLBY'S formula and compared to the empirical result. The calculated expected theoretical efficacy of a combination is determined using the formula of S. R. Colby: "Calculation of synergistic and antagonistic responses of herbicide combinations", Weeds 15 (1967), pages 20 to 22.

For combinations of two compounds, this formula is:

$$E = X + Y - \frac{X \cdot Y}{100}$$

and, correspondingly, for combinations of three herbicidally active compounds:

$$E = X + Y + Z + \frac{X \cdot Y \cdot Z}{10000} - \frac{XY + XZ + YZ}{100}$$

where
X=% damage by herbicide A at an application rate of x kg of ai/ha;
Y=% damage by herbicide B at an application rate of y kg of ai/ha;
Z=% damage by a further herbicide C at an application rate of z kg of ai/ha;
E=expected value, i.e. expected damage by herbicides A+B (or A+B+C) and x+y (or x+y+z) kg of ai/ha Synergistic effects were assumed to be present when the empirical value was greater than the expected value. Combinations of individual components of the same active compounds could also be prepared by using the sum formula.

However, in most cases the synergistic increase in activity is so high that the Colby criterion can be dispensed with; in these cases, the activity of the combination considerably surpasses the formal (calculated) sum of the activities of the individual compounds.

Particular attention has to be drawn to the fact that when the synergism between the active compounds employed here is assessed, the highly different application rates of the individual active compounds have to be taken into consideration. Thus, it is not expedient to compare the activities of the active compound combinations and those of the individual active compounds in each case at identical application rates. The amounts of active compounds that can be saved according to the invention become evident only from the superadditive increase in activity when using the combined applicational rates or by the reduction of the application rates of the two individual active compounds in the combinations in comparison to the individual active compounds, the activity remaining the same in each case.

TABLE 1

| Active compound(s) | g of ai/ha | LOLMU % control | TRZAW % damage |
|---|---|---|---|
| A)* | 5 | 8 | 0 |
|  | 10 | 73 | 0 |
|  | 20 | 97 | 0 |
|  | 40 | 98 | 0 |
|  | 80 | 99 | 0 |
| B1) | 18 | 0 | 0 |
|  | 37 | 0 | 0 |
|  | 75 | 8 | 0 |
| A)* + B1) | 5 + 18 | 75 (8 + 0) | 0 |
|  | 5 + 37 | 85 (8 + 0) | 0 |
|  | 10 + 18 | 95 (8 + 0) | 0 |
|  | 10 + 37 | 96 (8 + 0) | 0 |
|  | 20 + 18 | 99 (97 + 0) | 0 |
|  | 20 + 37 | 100 (97 + 0) | 0 |

LOLMU = *Lolium multiflorum*
TRZAW = *Triticum aestivum*
A)* = Sodium salt of

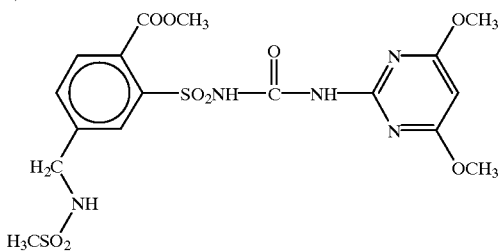

B1) = Puma S ® = mixture of fenoxaprop-P-ethyl and the safener fenchlorazole-ethyl = ethyl 1-(2,4-dichlorophenyl)-5-(trichloromethyl)-1H-1,2,4-triazole-3-carboxylate in a ratio of 2:1
(+) = effect of the individual substances (additive method)

TABLE 2

| Active compound(s) | g of ai/ha | AVEFA % control | TRZAW % damage |
|---|---|---|---|
| A) | 3.75 | 10 | 0 |
|  | 7.5 | 60 | 0 |
|  | 15 | 80 | 0 |
|  | 30 | 95 | 0 |
| B2) | 750 | 15 | 0 |
|  | 1500 | 60 | 0 |
|  | 3000 | 85 | 0 |
| A) + B2) | 3.75 + 750 | 88 (10 + 15) | 0 |
|  | 7.5 + 750 | 85 (60 + 15) | 0 |
|  | 15 + 750 | 95 (80 + 15) | 0 |
|  | 3.75 + 1500 | 96 (10 + 60) | 0 |
|  | 7.5 + 1500 | 99 (84)$^E$ | 0 |
|  | 15 + 1500 | 100 (92)$^E$ | 0 |

AVEFA = *Avena fabtua*
TRZAW = *Triticum aestivum*
A) =

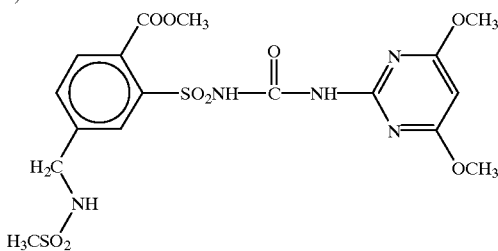

TABLE 2-continued

| Active compound(s) | g of ai/ha | AVEFA % control | TRZAW % damage |
|---|---|---|---|

B2) = isoproturon (Arelon ®)
(+) = effect of the individual substances
()$^E$ = expected value calculated according to Colby

TABLE 3

| Active compound(s) | g of ai/ha | GALAP % control | TRZAW % damage |
|---|---|---|---|
| A)* | 5 | 17 | 0 |
|  | 10 | 22 | 0 |
|  | 20 | 34 | 0 |
|  | 40 | 45 | 0 |
|  | 80 | 57 | 0 |
| B14) | 250 | 0 | 0 |
|  | 500 | 0 | 0 |
|  | 1000 | 5 | 0 |
| A)* + B14) | 5 + 1000 | 65 (17 + 5) | 0 |
|  | 10 + 250 | 65 (22 + 0) | 0 |
|  | 10 + 500 | 70 (22 + 0) | 0 |
|  | 10 + 1000 | 80 (22 + 5) | 0 |
|  | 20 + 250 | 75 (34 + 0) | 0 |
|  | 20 + 500 | 80 (34 + 0) | 0 |
|  | 20 + 1000 | 85 (34 + 5) | 0 |

GALAP = *Galium aparine*
TRZAW = *Triticum aestivum*
A)* = Sodium salt of

B14) = Sodium salt of MCPA
(+) = effect of the individual substances

TABLE 4

| Active compound(s) | g of ai/ha | GALAP % control | TRZAW % damage |
|---|---|---|---|
| A)* | 5 | 17 | 0 |
|  | 10 | 22 | 0 |
|  | 20 | 34 | 0 |
|  | 40 | 45 | 0 |
|  | 80 | 57 | 0 |
| B19) | 63 | 0 | 0 |
|  | 125 | 3 | 0 |
|  | 250 | 10 | 0 |
|  | 500 | 18 | 0 |
| A)* + B19) | 10 + 500 | 75 (22 + 18) | 0 |
|  | 20 + 125 | 70 (34 + 3) | 0 |
|  | 20 + 250 | 77 (34 + 10) | 0 |
|  | 20 + 500 | 83 (34 + 18) | 0 |
|  | 40 + 63 | 70 (45 + 0) | 0 |
|  | 40 + 125 | 75 (45 + 3) | 0 |
|  | 40 + 250 | 82 (45 + 10) | 0 |
|  | 40 + 500 | 87 (45 + 18) | 0 |
|  | 80 + 63 | 80 (57 + 0) | 0 |
|  | 80 + 125 | 80 (57 + 3) | 0 |
|  | 80 + 250 | 88 (57 + 10) | 0 |
|  | 80 + 500 | 93 (57 + 18) | 0 |

GALAP = *Galium aparine*
TRZAW = *Triticum aestivum*
A)* = Sodium salt of

TABLE 4-continued

| Active compound(s) | g of ai/ha | GALAP % control | TRZAW % damage |
|---|---|---|---|

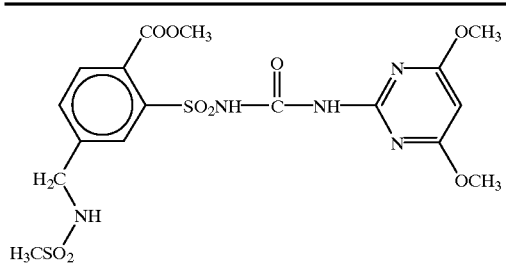

B19) = ioxynil
(+) = effect of the individual substances

TABLE 5

| Active compound(s) | g of ai/ha | GALAP % control | TRZAW % damage |
|---|---|---|---|
| A)* | 5 | 17 | 0 |
| | 10 | 22 | 0 |
| | 20 | 34 | 0 |
| | 40 | 45 | 0 |
| | 80 | 57 | 0 |
| B22) | 4 | 0 | 0 |
| | 8 | 0 | 0 |
| | 15 | 8 | 0 |
| | 30 | 8 | 0 |
| A)* + B22) | 5 + 30 | 45 (17 + 8) | 0 |
| | 10 + 15 | 68 (22 + 8) | 0 |
| | 10 + 30 | 65 (22 + 8) | 0 |
| | 20 + 4 | 48 (34 + 0) | 0 |
| | 20 + 8 | 65 (34 + 0) | 0 |
| | 20 + 15 | 73 (34 + 8) | 0 |
| | 20 + 30 | 78 (34 + 8) | 0 |
| | 40 + 4 | 55 (45 + 0) | 0 |
| | 40 + 8 | 65 (45 + 0) | 0 |
| | 40 + 15 | 75 (45 + 8) | 0 |
| | 40 + 30 | 80 (45 + 8) | 0 |

GALAP = Galium aparine
TRZAW = Triticum aestivum
A)* = Sodium salt of

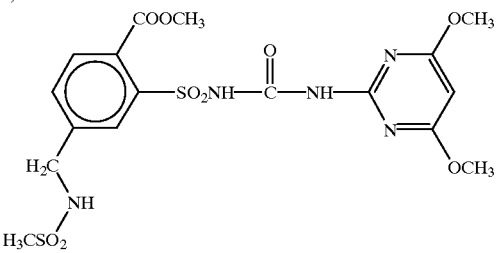

B22) = fluoroglycofen-ethyl (Compete ®)
(+) = effect of the individual substances (additive method)

TABLE 6

| Active compound(s) | g of ai/ha | GALAP % control | TRZAW % damage |
|---|---|---|---|
| A)* | 5 | 17 | 0 |
| | 10 | 22 | 0 |
| | 20 | 34 | 0 |
| | 40 | 45 | 0 |
| | 80 | 57 | 0 |
| B29) | 13 | 0 | 0 |
| | 25 | 0 | 0 |
| | 50 | 5 | 0 |
| | 100 | 5 | 0 |

TABLE 6-continued

| Active compound(s) | g of ai/ha | GALAP % control | TRZAW % damage |
|---|---|---|---|
| A)* + B29) | 5 + 100 | 60 (17 + 5) | 0 |
| | 10 + 100 | 65 (22 + 5) | 0 |
| | 20 + 50 | 68 (22 + 5) | 0 |
| | 20 + 100 | 70 (34 + 5) | 0 |
| | 40 + 25 | 68 (45 + 0) | 0 |
| | 40 + 50 | 75 (45 + 5) | 0 |
| | 40 + 100 | 82 (45 + 5) | 0 |
| | 80 + 13 | 63 (57 + 0) | 0 |
| | 80 + 25 | 75 (57 + 0) | 0 |
| | 80 + 50 | 88 (57 + 5) | 0 |
| | 80 + 100 | 98 (57 + 5) | 0 |

GALAP = Galium aparine
TRZAW = Triticum aestivum
A)* = Sodium salt of

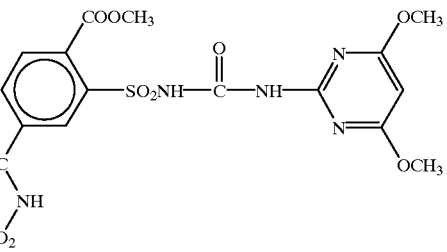

B29) = diflufenican
(+) = effect of the individual substances (additive method)

TABLE 7

| Active compound(s) | g of ai/ha | OXAPC % control | TRZAW % damage |
|---|---|---|---|
| A)* | 5 | 0 | 0 |
| | 10 | 7 | 0 |
| | 20 | 20 | 0 |
| B42) | 5 | 27 | 0 |
| | 10 | 59 | 0 |
| A)* + B42) | 5 + 5 | 93 (0 + 27) | 0 |
| | 5 + 10 | 94 (0 + 59) | 0 |
| | 10 + 5 | 100 (7 + 27) | 0 |

OXAPC = Oxalis pes-carprae
TRZAW = Triticum aestivum (summer wheat)
A)* = Sodium salt of

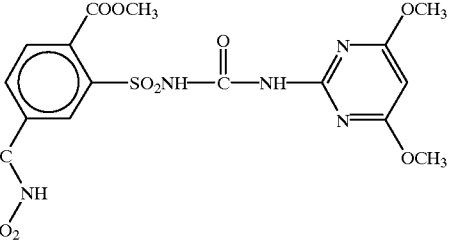

B42) = sodium salt of methyl 4-iodo-2-[3-(4-methoxy-6-methyl-1,3,5-triazin-2-yl)ureidosulfonyl]benzoate
(+) = effect of the individual substances (additive method)

TABLE 7a

| Active compound(s) | g of ai/ha | AVSSP % control | LOLSP % control | TRZAW % damage | TRZD % damage |
|---|---|---|---|---|---|
| A) | 10 | 70 | 29 | 4 | 3 |
| | 20 | 87 | 69 | 11 | 6 |
| B42) | 5 | 29 | 46 | 2 | 2 |
| | 10 | 31 | 88 | 3 | 3 |
| A) + B42) | 10 + 5 | 86 (78)[E] | 81 (29 + 27) | 14 | 7 |

TABLE 7a-continued

| Active compound(s) | g of ai/ha | AVSSP % control | LOLSP % control | TRZAW % damage | TRZD % damage |
|---|---|---|---|---|---|

AVSSP = *Avena ssp.*
LOLSP = *Lolium ssp.*
TRZAW = *Triticum aestivum* (summer wheat)
TRZD = *Triticum durum*
A) =

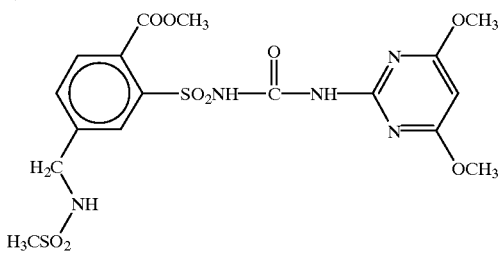

B42) = sodium salt of methyl 4-iodo-2-[3-(4-methoxy-6-methyl-1,3,5-triazin-2-yl)ureidosulfonyl]benzoate
(+) = effect of the individual substances (additive method)
()$^E$ = expected value calculated according to Colby

TABLE 7b

| Active compound(s) | g of ai/ha | APSV % control | GALAP % control | TRZAW % damage | TRZD % damage |
|---|---|---|---|---|---|
| A) | 10 | 68 | 10 | 4 | 3 |
|    | 20 | 78 | 13 | 11 | 6 |
| B42) | 5 | 0 | 90 | 2 | 2 |
|    | 10 | 5 | 98 | 3 | 3 |
| A) + B42) | 10 + 5 | 80 (68 + 0) | 100 (91)$^E$ | 14 | 7 |

APSV = *Apera spica venti*
GALAP = *Galium aparine*
TRZAW = *Triticum aestivum* (summer wheat)
TRZD = *Triticum durum*
A) =

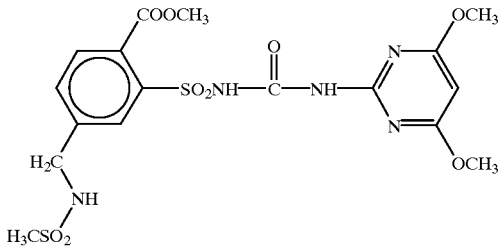

B42) = sodium salt of methyl 4-iodo-2-[3-(4-methoxy-6-methyl-1,3,5-triazin-2-yl)ureidosulfonyl]benzoate
(+) = effect of the individual substances (additive method)
()$^E$ = expected value calculated according to Colby

TABLE 7c

| Active compound(s) | g of ai/ha | POLGC % control | CHPA % control | TRZAW % damage | TRZD % damage |
|---|---|---|---|---|---|
| A) | 10 | 12 | 5 | 4 | 3 |
|    | 20 | 24 | 50 | 11 | 6 |
| B42) | 5 | 65 | 0 | 2 | 2 |
|    | 10 | 83 | 65 | 3 | 3 |
| A) + B42) | 10 + 5 | 90 (12 + 62) | 94 (5 + 0) | 14 | 7 |

POLGC = *Polygonum conv.*
CHPA = *Chenopodium alb.*
TRZAW = *Triticum aestivum* (summer wheat)
TRZD = *Triticum durum*
A) =

TABLE 7c-continued

| Active compound(s) | g of ai/ha | POLGC % control | CHPA % control | TRZAW % damage | TRZD % damage |
|---|---|---|---|---|---|

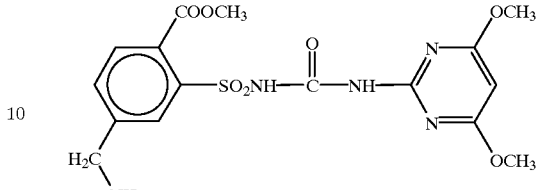

B42) = sodium salt of methyl 4-iodo-2-[3-(4-methoxy-6-methyl-1,3,5-triazin-2-yl)ureidosulfonyl]benzoate
(+) = effect of the individual substances (additive method)
()$^E$ = expected value calculated according to Colby

TABLE 7d

| Active compound(s) | g of ai/ha | PAPRH % control | PHYAN % control | TRZAW % damage | TRZD % damage |
|---|---|---|---|---|---|
| A) | 10 | 0 | 38 | 4 | 3 |
|    | 20 | 50 | 50 | 11 | 6 |
| B42) | 5 | 0 | 0 | 2 | 2 |
|    | 10 | 83 | 65 | 3 | 3 |
| A) + B42) | 10 + 5 | 88 (0 + 0) | 94 (5 + 0) | 14 | 7 |

PAPRH = *Paphaver rhoeas*
PHYAN = *Physalis angulata*
TRZAW = *Triticum aestivum* (summer wheat)
TRZD = *Triticum durum*
A) =

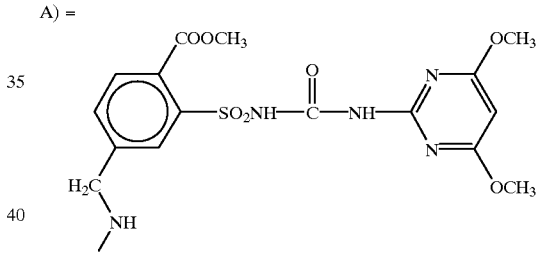

B42) = sodium salt of methyl 4-iodo-2-[3-(4-methoxy-6-methyl-1,3,5-triazin-2-yl)ureidosulfonyl]benzoate
(+) = effect of the individual substances (additive method)
()$^E$ = expected value calculated according to Colby

TABLE 7e

| Active compound(s) | g of ai/ha | BRASN % control | LAMPU % control | TRZAW % damage | TRZD % damage |
|---|---|---|---|---|---|
| A) | 10 | 5 | 47 | 4 | 3 |
|    | 20 | 50 | 48 | 11 | 6 |
| B42) | 5 | 0 | 80 | 2 | 2 |
|    | 10 | 65 | 95 | 3 | 3 |
| A) + B42) | 10 + 5 | 94 (5 + 0) | 100 (90)$^E$ | 14 | 7 |
| Active compound(s) | g of ai/ha | KOSC % control | STLMD % control | TRZAW % damage | TRZD % damage |
| A) | 10 | 58 | 80 | 4 | 3 |
|    | 20 | 68 | 90 | 11 | 6 |
| B42) | 5 | 94 | 98 | 2 | 2 |
|    | 10 | 98 | 100 | 3 | 3 |
| A) + B42) | 10 + 5 | 98 (97)$^E$ | 100 (99)$^E$ | 14 | 7 |

BRASN = *Brassica napus*
LAMPU = *Lamicum purpureum*
KOSC = *Kochia scorpium*
STLMD = *Stellaria media*

TABLE 7e-continued

TRZAW = *Triticum aestivum* (summer wheat)
TRZD = *Triticum durum*
A) =

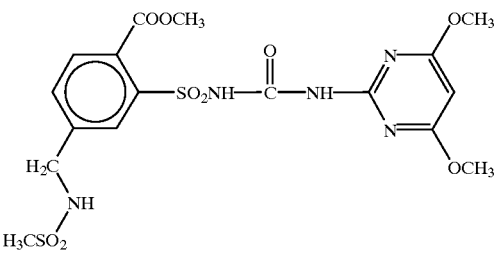

B42) = sodium salt of methyl 4-iodo-2-[3-(4-methoxy-6-methyl-1,3,5-triazin-2-yl)ureidosulfonyl]benzoate
(+) = effect of the individual substances (additive method)
()$^E$ = expected value calculated according to Colby

TABLE 8

| Active compound(s) | g of ai/ha | PHAMI | DESSO | CAPBP |
|---|---|---|---|---|
|  |  | % control |  | % damage |
| A) | 10 | 30 | 80 | 0 |
| B46) | 270 | 25 | 0 | 15 |
|  | 450 | 63 | 0 | 18 |
| A) + B46) | 10 + 270 | 68 (30 + 25) | 99 (80 + 0) | 73 (0 + 15) |

PHAMI = *Phalaris minor*
DESSO = *Descurainia richardssonii*
CAPBP = *Capsella bursa pastoris*
A) =

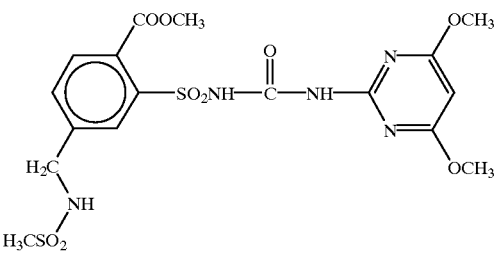

B46) = glufosinate-ammonium
(+) = % effect of the individual active compounds (addition)

TABLE 9

| Active compound(s) | g of ai/ha | AVEFA % effect sensitive | AVEFA % effect resistant |
|---|---|---|---|
| A) | 10 | 72 | 80 |
|  | 20 | 95 | 95 |
| B1) | 100 | 90 | 35 |
| A) + B1) | 10 + 100 | 98 (97)$^E$ | 97 (87)$^E$ |

AVEFA = *Avena Fatua*
sensitive = AVEFA populations which have not developed any resistance
resistant = AVEFA populations which have already developed a resistance
A) =

TABLE 9-continued

| Active compound(s) | g of ai/ha | AVEFA % effect sensitive | AVEFA % effect resistant |
|---|---|---|---|

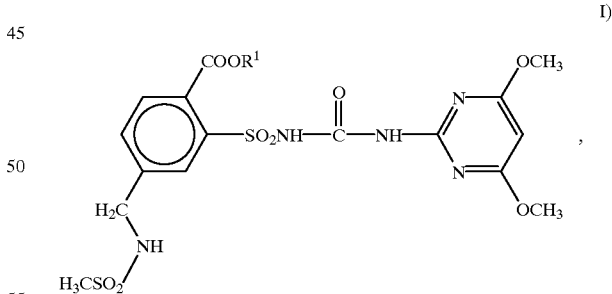

B1) = Puma S ® = mixture of fenoxaprop-P-ethyl and the safener fenchlorazole-ethyl = ethyl 1-(2,4-dichlorophenyl)-5-(trichloromethyl)-1H-1,2,4-triazole-3-carboxylate in a ratio of 2:1
()$^E$ = expected value calculated according to Colby The examples show that the individual active compounds allow efficient control of individual weeds only in high dosages. If the combination partners are applied in low dosages, they generally only have low activity, far less than required in practice. Good effects against all of the weed species examined can only be obtained by joint application of the active compounds. Here, the additive effect of the individual components was surpassed considerably, i.e. their required level of control is achieved by significantly lower application rates. Owing to these effects, the activity spectrum is widened significantly. Even populations of harmful plants which have already developed resistance against individual herbicides are more effectively controlled by the combinations according to the invention (cf. Table 9).

The crop safety, assessed in the form of damage, is not affected negatively, i.e. the combinations can be judged to be fully selective.

Further advantages and embodiments of the invention are evident from the patent claims below.

What is claimed is:
1. A herbicidal composition, comprising
   A) at least one compound from the group of the substituted phenylsulfonylureas of the formula I and agriculturally acceptable salts thereof

I)

in which
   R$^1$ is (C$_1$–C$_8$)-alkyl, (C$_3$–C$_4$)alkenyl, or (C$_3$–C$_4$)-alkynyl or (C$_1$–C$_4$)-alkyl which is mono- to tetra-substituted by radicals selected from the group consisting of halogen and (C$_1$–C$_2$)-alkoxy, and
   B) at least one herbicidally active compound selected from the group of the compounds consisting of
   Ba) herbicides which have selective activity against grasses in cereals,
   Bb) herbicides which have selective activity against dicotyledons in cereals, Bc) herbicides which have selective activity against grasses and dicotyledons in cereals and Bd) herbicides which are active against weed grasses and broad-leaved weeds and which are nonselective in non-cop areas or perennial crops (plantations) and/or selective in transgenic crops.

2. The composition as claimed in claim 1, wherein in the herbicide of the formula (1) or the salt thereof $R^1$ is methyl, ethyl, n- or isopropyl, n-, tert-, 2-butyl or isobutyl, n-pentyl, isopentyl, n-exyl, isohexyl, 1,3-dimethylbutyl, n-heptyl, 1-methylhexyl or 1,4-dimethylpentyl.

3. The composition as claimed in claim 1, wherein in the herbicide of the formula (I) or the salt thereof $R^1$ is methyl.

4. The composition as claimed in claim 1, wherein the salt of the herbicide of the formula (I) is formed by replacing the hydrogen of the —SO$_2$—NHCO— group by a cation selected from the group of the alkali metals, alkaline earth metals and ammonium.

5. The composition as claimed in claim 1, which comprises as herbicides of Ba which have selective activity against grasses in cereals and are selected from the group comprising the 2(4aryloxyphenoxy)propionic acids, or esters sulfonylureas, cyclohexanedione oximes, imidazolinones and difenzoquat.

6. The composition as claimed in claim 1, which comprises as herbicides of Ba which have selective activity against grasses in cereals and are selected from the group consisting of

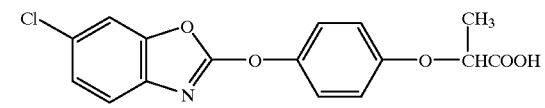

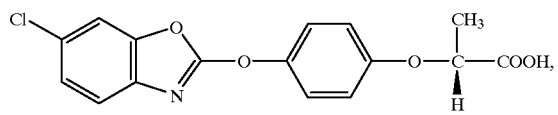

B2) isoproturon

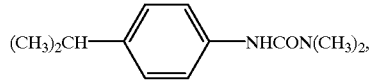

B3) diclofop

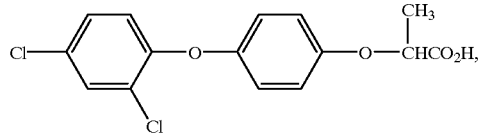

-continued

B4) clodinafop

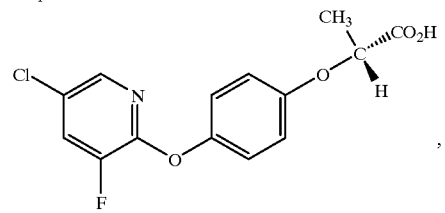

B5) mixtures of B4) and cloquintocet

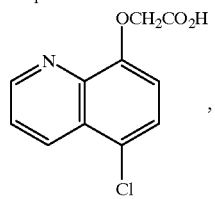

B6) chlorotoluron

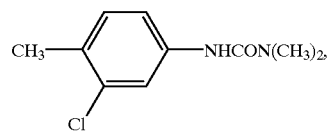

B7) methabenzthiazuron

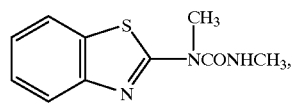

B8) imazamethabenz

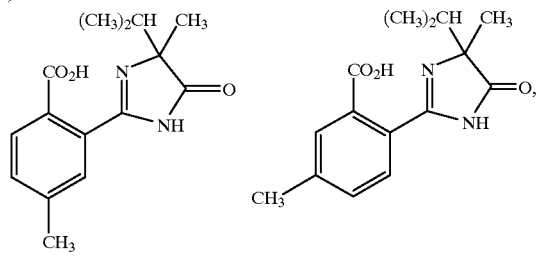

B9) tralkoxydim

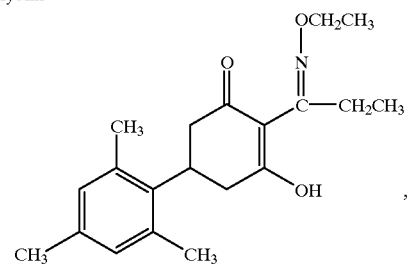

B10) difenzoquat

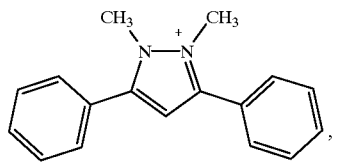

-continued

B11) flamprop, flamprop-M

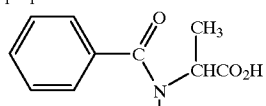

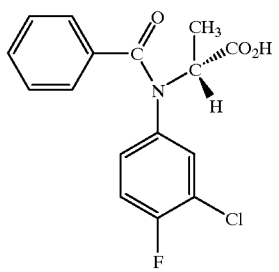
and

B12) pendimethalin

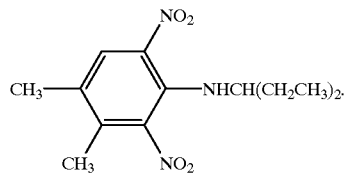

7. The composition as claimed in claim 6, which comprises as herbicides of fenoxaprop-P-ethyl, isoproturon and/or mixtures of clodinafop-propargyl with cloquintocet-mexyl.

8. The composition as claimed in claim 1 which comprises as herbicides of Bb which have selective activity against dicotyledons in cereals and are selected from the group comprising aryloxyalkylcarboxylic acids, hydroxybenzonitriles, diphenyl ethers, azoles pyrazoles, diflufenican and bentazone.

9. The composition as claimed in claim 1, which comprises as herbicides of Bb which have selective activity against dicotyledons in cereals and are selected from the group consisting of B13) mecoprop, mecoprop-P

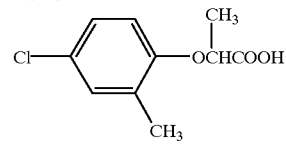

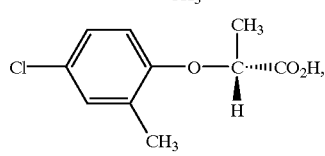

-continued

B14) MCPA

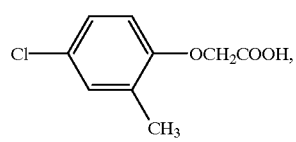

B15) dichlorprop, dichlorprop-P

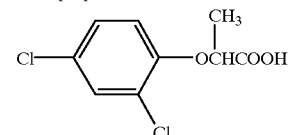

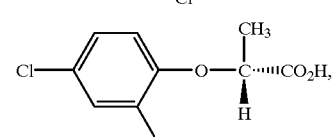

B16) 2, 4-D

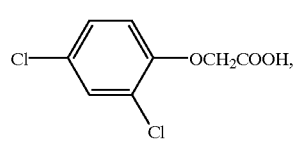

B17) dicamba

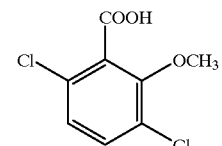
and

B18) fluroxypyr

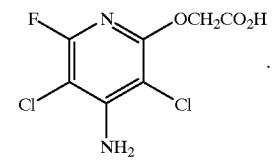

10. The composition as claimed in claim 1 which comprises as herbicides of Bb which have selective activity against dicotyledons in cereals and are selected from the group consisting of B19) ioxynil

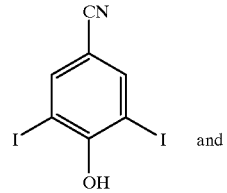
and

B20) bromoxynil

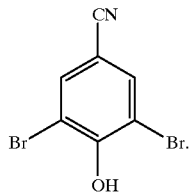

11. The composition as claimed in claim 1, which comprises as herbicides of Bb which have selective activity against dicotyledons in cereals and are selected from the group consisting of B21) bifenox
   methyl 5-(2,4-dichlorophenoxy)-2-nitrobenzoate

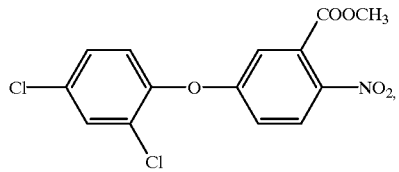

B22) fluoroglycofen

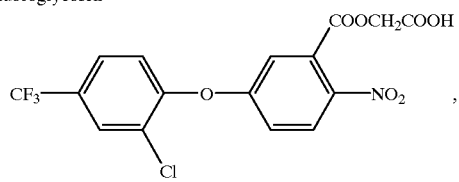

B23) lactofen

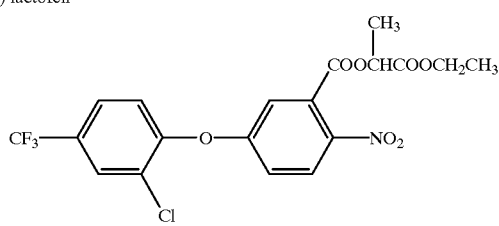

B24) fomesafen

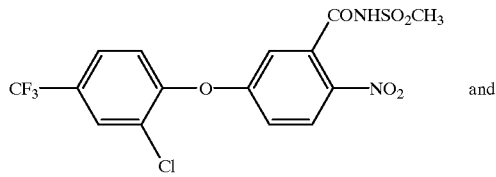 and

B25) oxyfluorfen

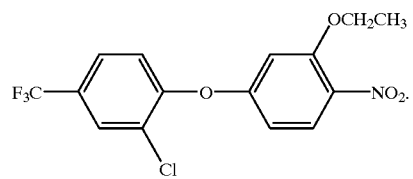

12. The composition as claimed in claim 1 which comprises
   as herbicides Bb which have selective activity against dicotyledons in cereals and are selected from the group consisting of

B26) ET 751

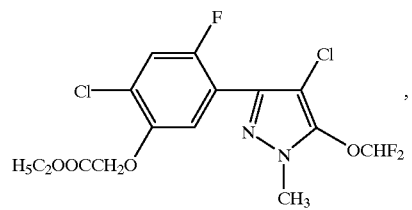

B27) azoles of the formula II

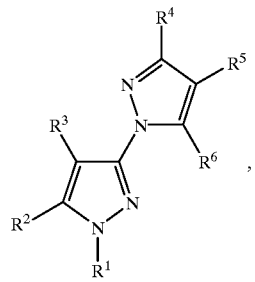

(II)

in which

R$^1$ is (C$_1$–C$_4$)-alkyl

R$^2$ is (C$_1$–C$_4$)alkyl, (C$_1$–C$_4$)-alkylthio or (C$_1$–C$_4$)-alkoxy, each of which may be substituted by one or more halogen atoms, or R$^1$ and R$^2$ together form the group (CH$_2$)$_m$ where m =3 or 4, R$^3$ is hydrogen or halogen R$^4$ is hydrogen or (C$_1$–C$_4$)-alkyl, R$^5$ is hydrogen, nitro, cyano or one of the groups —COOR$^7$, —C(=X)NR$^7$R$^8$ or —C(=X)R$^{10}$, X=O or S R$^6$ is hydrogen, halogen, cyano, (C$_1$–C$_4$)-alkyl, (C$_1$–C$_4$)-alkylthio or —NR$^{11}$R$^{12}$ , R$^7$ and R$^8$ are identical or different and each is hydrogen or (C$_1$–C$_4$)-alkyl, or R$^7$ and R$^8$ join with the nitrogen to which they are attached to form a saturated 5- or 6-membered carbocyclic ring, R$^{10}$ is hydrogen or (C$_1$–C$_4$)-alkyl, the latter optionally being substituted by one or more halogen atoms, and R$^{11}$ and R$^{12}$ are identical or different and each is hydrogen, (C$_1$–C$_4$)-alkyl or (C$_1$–C$_4$)-alkoxycarbonyl, where R$^{11}$ and R$^{12}$ may join with the nitrogen to which they are attached to form a 3-, 5- or 6-membered carbocyclic or aromatic ring in which one carbon atom may be replaced by an oxygen atom; and

B28) F8426

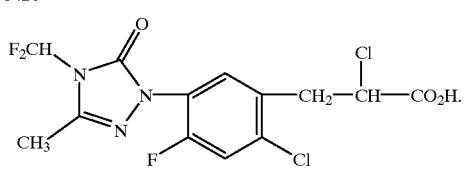

13. The composition as claimed in claim 1, which comprises.

as herbicide of Bb

B29) diflufenican

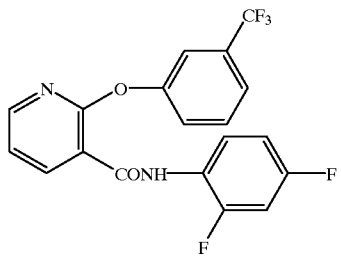

which has selective activity against dicotyledons in cereals.

14. The composition as claimed in claim 1 which comprises as herbicide Bb

B30) bentazone

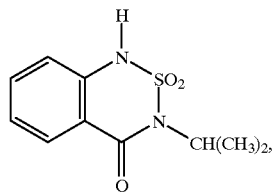

which has selective activity against dicotyledons in cereals and/or maize.

15. The composition as claimed in claim 9, which comprises herbicide MCPA diflufenican, ioxynil and/or fluoroglycofen.

16. The composition as claimed in claim 1, which comprises as herbicides Bc which have selective activity against grasses and dicotyledons in cereals and are selected from the group which -comprises triazine derivatives, (thio)carbamates, furanones and sulfonylureas selected from the sulfonylureas of formula I.

17. The composition as claimed in claim 1, which comprises herbicide selected from the group comprising B31) metribuzin

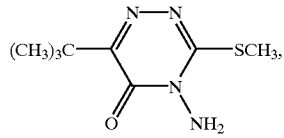

B32) metosulam

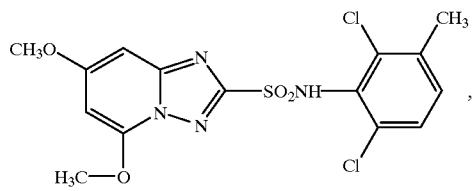

B32a) flupoxam

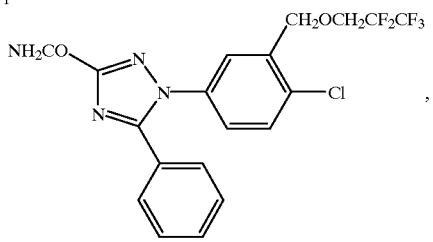

B33) prosulfocarb

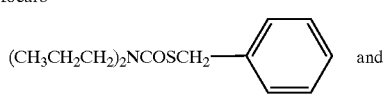

and

B34) flurtamone

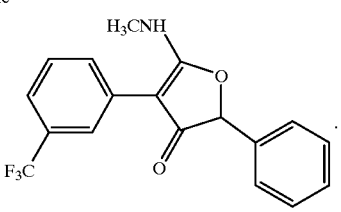

18. The composition as claimed in claim 1, which comprises as herbicides group B selected from the group which includes B35) amidosulfuron

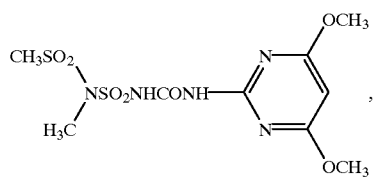

B36) metsulfuron

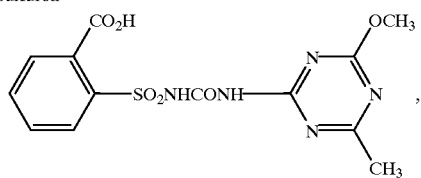

B37) tribenuron

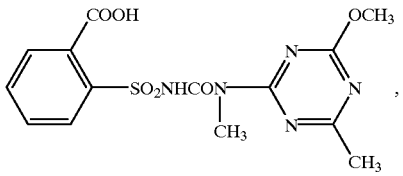

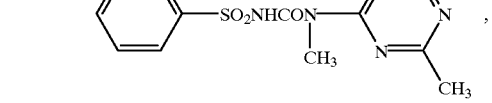

-continued

B38) thifensulfuron

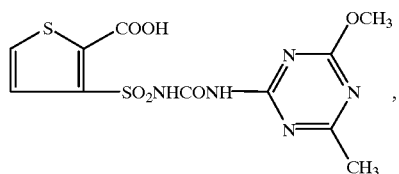

B39) triasulfuron

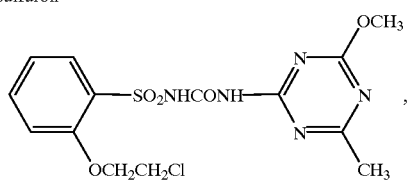

B40) chlorsulfuron

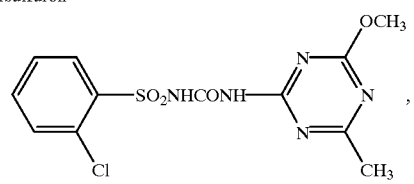

B41) sulfonylureas of the formula III

III)

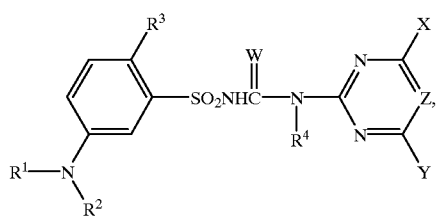

in which

R$^1$ is methyl, ethyl, n-propyl, isopropyl or allyl,

R$^2$ is CO—R$^5$, COOR$^6$, CO—NR$^8$R$^9$, CS—NR$^{10}$R$^{11}$, SO$_2$R$^{14}$ or SO$_2$NR$^{15}$R$^{16}$,

R$^3$ is COR$^{17}$, COOR$^{18}$, CONR$^{19}$R$^{20}$ or CO—ON=CR$^{22}$R$^{23}$,

R$^4$ is hydrogen or (C$_1$–C$_4$)-alkyl,

R$^5$ is hydrogen, (C$_1$–C$_4$)-alkyl, (C$_1$–C$_2$)haloalkyl, cyclopropyl, phenyl, benzyl or heteroaryl having 5 or 6 ring atoms, the last 3 radicals being unsubstituted or substituted by one or more halogen atoms, R$^6$ is (C$_1$–C$_4$)-alkyl, allyl, propargyl or cyclopropyl, R$^8$ is hydrogen, (C$_1$–C$_4$)-alkyl, (C$_1$–C$_4$)-haloalkyl or (C$_1$–C$_4$-alkoxy)-carbonyl, R$^9$–R$^{11}$ are independently of one another identical or different H or (C$_1$–C$_4$)-alkyl, R$^{14}$ is (C$_1$–C$_4$)-alkyl, R$^{15}$ and R$^{16}$ are independently of one another identical or different hydrogen or (C$_1$–C$_4$)-alkyl, R$^{17}$ is hydrogen, (C$_1$–C$_4$)-alkyl, (C$_1$–C$_4$)-haloalkyl, (C$_3$–C$_6$)cycloalkyl, phenyl or heteroaryl, the last two radicals being unsubstituted or substitutes R$^{18}$ is hydrogen, (C$_1$–C$_4$)-alkyl, (C$_2$–C$_6$)-alkenyl or (C$_2$–C$_6$)-alkynyl, the last three radicals being unsubstituted or substituted by one or more radicals selected from the group consisting of halogen, (C$_1$–C$_4$)-alkoxy, (C$_1$–C$_4$)-alkylthio and NR$^{31}$R$^{32}$, or (C$_3$–C$_6$)-cycloalkyl or (C$_3$–C$_6$)-cycloalkyl(C$_1$–C$_3$)-alkyl, R$^{19}$ is analogous to R$^8$, R$^{20}$ is analogous to R$^9$, R$^{22}$ and R$^{23}$ are independently of one another identical or different hydrogen or (C$_1$–C$_2$)-alkyl, R$^{31}$ and R$^{32}$ are independently of one another identical or different hydrogen or (C$_1$–C$_4$)alkyl, W is oxygen or sulfur, X is (C$_1$–C$_4$)alkyl, (C$_1$–C$_4$)-alkoxy, (C$_1$–C$_4$)-haloalkyl, (C$_1$–C$_4$)-alkylthio, halogen or mono- or di-C$_1$–C$_2$-alkyl)-amino, Y is (C$_1$–C$_4$)-alkyl, (C$_1$–C$_4$)-alkoxy, (C$_1$–C$_4$)-haloalkyl or (C$_1$–C$_4$)-alkylthio, and X is CH or N, B42) sulfonylureas of the formula IV and agriculturally tolerable and acceptable salts thereof

IV)

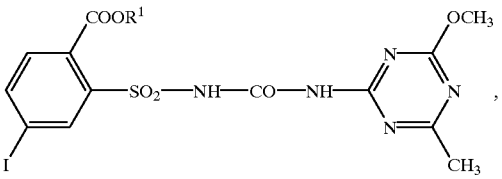

which

R$^1$ is (C$_1$–C$_8$)-alkyl, (C$_3$–C$_4$)-alkenyl, or (C$_3$–C$_4$)alkynyl or (C$_1$–C$_4$)-alkyl which is mono- to tetrasubstituted by radicals selected from the group consisting of halogen and (C$_1$–C$_2$)-alkoxy, where in the herbicide of the formula (IV) or the salt thereof.

and where those salts have favorable activity where the salt of the herbicide of the formula (IV) is formed by replacing the hydrogen of the —SO$_2$—NHCO— group by a cation selected from the group of the alkali metals, alkaline earth metals and ammonium, B43) flupyrsulfuron (DPX-KE459)

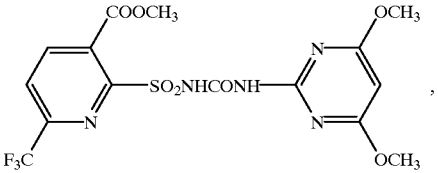

B44) MON 48500 and B45) sulfosulfuron (MON37500)

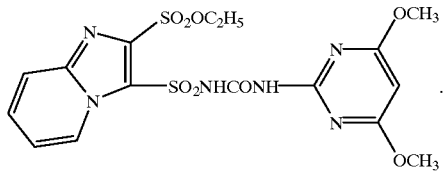

19. The composition as claimed in claim 17, which comprises as herbicide of group B the sodium salt of methyl 4-iodo-2-[3-(4-methoxy-6-methyl-1,3,5-triazin-2-yl)ureidosulfonyl]benzoate.

20. The composition as claimed in claim 1, which comprises as herbicides of Bd which are active against weed grasses and broad-leaved weeds and which are nonselective in non-crop areas or perennial crops (plantations) and/or selected in transgenic crops and which are selected from the group consisting of B46) glufosinate, glufosinate-P

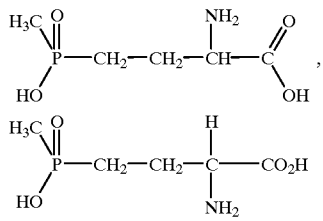

and
B47) glyphosate

21. The composition as claimed in claim 20, which comprises
as herbicide of group B glufosinate-ammonium.
22. The composition as claimed in claim 1, which comprises
a synergistically effective amount of a combination of the compounds of the formula I or salts thereof (group A compound) with compounds selected from group B.
23. The composition as claimed in claim 1, which comprises the compounds of the formula I or salts thereof (group A compounds) and the compounds selected from group B in a weight ratio of 1:2500 to 20:1.
24. The composition as claimed in claim 1, which comprises
0.1 to 99% by weight of the active compounds A and B, in addition to customary formulation auxiliaries.
25. A process for preparing a composition which comprises
mixing the compounds of the formula I or salts thereof (group A compounds) with one or more compounds of group B and, if appropriate, with one or more compounds of group C using a customary crop protection formulation selected from the group consisting of wettable powders, emulsifiable concentrates, aqueous solutions, emulsions, sprayable solutions (tank-mix), oil- or water-based dispersions, suspoemulsions, dusts, seed dressings, granules for soil application or application by broadcasting, water-dispersible granules, ULV formulations, microcapsules and waxes.
26. A method for controlling undesirable plants, which comprises applying a herbicidally effective amount of one of the combinations of active compounds A+B as claimed in claim 1 onto the plants or the cultivated area.
27. The method as claimed in claim 26, wherein
the application rate for the compounds of the formula (I) or salts thereof (group A compounds) is from 0.1 to 100 g of ai/ha, and the application rates for the compounds of group B are from 1 to 5000 g of ai/ha.
28. The method as claimed in claim 26, wherein
the active compounds of groups A and B are applied simultaneously or at different times in a weight ratio of 1:2500 to 20:1.
29. The method as claimed in claim 26, wherein
the combinations are employed for the selective control of undesirable plants.
30. The method as claimed in claim 29, wherein
the combinations are employed in transgenic crops.
31. The method as claimed in claim 30, wherein
the combinations are employed in cereals, maize, rice, sugar cane, crop plantations, meadows or pasture land.
32. The method as claimed in claim 26, wherein
the combinations are employed in crops of useful plants.
33. The method as claimed in claim 26, wherein
the combinations are employed in non-crop areas.
34. The method as claimed in claim 26, wherein
harmful plants which are usually resistant are controlled.
35. The composition as claimed in claim 4, wherein the alkali metal is sodium.
36. The composition of claim 18, wherein $R^1$ of the sulfonylurea of formula TV (B42) is methyl.
37. The composition of claim 18, wherein the alkali metal is sodium.
38. The composition of claim 27, wherein the application rate for the compounds of the formula (T) or salts thereof is from 2 to 40 g of ai/ha.

* * * * *